(12) United States Patent
Lipsky et al.

(10) Patent No.: US 7,273,699 B2
(45) Date of Patent: Sep. 25, 2007

(54) METHODS FOR DETECTING NUCLEIC ACID SEQUENCE VARIATION

(75) Inventors: Robert H. Lipsky, Kensington, MD (US); Chiara Mazzanti, Washington, DC (US); David Goldman, Potomac, MD (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 330 days.

(21) Appl. No.: 10/206,561

(22) Filed: Jul. 25, 2002

(65) Prior Publication Data

US 2003/0157507 A1 Aug. 21, 2003

Related U.S. Application Data

(60) Provisional application No. 60/353,941, filed on Jan. 31, 2002.

(51) Int. Cl.
*C12Q 1/68* (2006.01)
*C12P 19/34* (2006.01)
(52) U.S. Cl. .......................... 435/6; 435/91.2
(58) Field of Classification Search .......... 435/6, 435/91.1, 91.2
See application file for complete search history.

(56) References Cited

U.S. PATENT DOCUMENTS 6,346,386 B1 * 2/2002 Elenitoba-Johnson .......... 435/6
6,458,584 B1 * 10/2002 Mirzabekov et al. ..... 435/287.2

OTHER PUBLICATIONS

Taparowsk et al. GenBank Accession No. L00041. National Center for Biotechnology Information, NIH, NLM (Bethesda, MD, USA) Jan. 8, 1995.*
McKie et al. GenBank Accession No. AF352795. National Center for Biotechnology Information, NIH, NLM (Bethesda, MD, USA) Apr. 10, 2001.*
Hermann (Clinical Chemistry. 2000. 46: 425-428.*
Akey et al., "Melting Curve Analysis of SNPs (McSNP®): a Gel-Free and Inexpensive Approach for SNP Genotyping," *BioTechniques* 30:358-367 (2001).
Aoshima et al., "Rapid Detection of Deletion Mutations in Inherited Metobolic Diseases by Melting Curve Analysis with LightCycler," *Clin. Chem.* 46:119-131 (2000).
Elenitoba-Johnson et al., "Solution-Based Scanning for Single-Base Alterations Using a Double-Stranded DNA Binding Dye and Fluorescence-Melting Profiles," *Am. J. Pathol.* 159:845-853 (2001).
Lipsky et al., "DNA Melting Analysis for Detection of Single Nucleotide Polymorphisms," *Clin. Chem.* 47:635-644 (2001).
Marziliano et al., "Melting Temperature Assay for a *UGT1A* Gene Variant in Gilbert Syndrome," *Clin. Chem.* 46:423-425 (2000).
Ririe et al., "Product Differentiation by Analysis of DNA Melting Curves during the Polymerase Chain Reaction," *Analy. Biochem.* 245:154-160 (1997).

* cited by examiner

Primary Examiner—Carla J. Myers
(74) Attorney, Agent, or Firm—Klarquist Sparkman, LLP

(57) ABSTRACT

Sequence variations, such as polymorphisms, are detected by detecting differences between or among melting profiles of plural nucleic acids. Melting profiles are produced by observing the nucleic acids during a temperature change over a period of time. If the nucleic acids are diluted into solutions for analysis, the nucleic acid concentrations between or among the solutions can be substantially the same. The melting profiles and sequence variation can be used to identify changes in a wild-type nucleic acid sequence, such as a single-nucleotide polymorphism (SNP), a small insertion or deletion, or a small inversion.

44 Claims, 17 Drawing Sheets

SEQUENCE LISTING

<160> NUMBER OF SEQ ID NOS: 24

<210> SEQ ID NO 1
<211> LENGTH: 15
<212> TYPE: DNA
<213> ORGANISM: Artificial Sequence
<220> FEATURE:
<223> OTHER INFORMATION: Fragments of the human HTR2A sequence

<400> SEQUENCE: 1
ttaactctgg agaag                                                      15

<210> SEQ ID NO 2
<211> LENGTH: 15
<212> TYPE: DNA
<213> ORGANISM: Artificial Sequence
<220> FEATURE:
<223> OTHER INFORMATION: Fragments of the human HTR2A sequence

<400> SEQUENCE: 2
ttaactccgg agaag                                                      15

<210> SEQ ID NO 3
<211> LENGTH: 25
<212> TYPE: DNA
<213> ORGANISM: Artificial Sequence
<220> FEATURE:
<223> OTHER INFORMATION: Fragments of the human HTR2A sequence

<400> SEQUENCE: 3
tgactttaac tctggagaag ctaac                                           25

<210> SEQ ID NO 4
<211> LENGTH: 25
<212> TYPE: DNA
<213> ORGANISM: Artificial Sequence
<220> FEATURE:
<223> OTHER INFORMATION: Fragments of the human HTR2A sequence

<400> SEQUENCE: 4
tgactttaac tccggagaag ctaac                                           25

<210> SEQ ID NO 5
<211> LENGTH: 20
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 5
accaggctct acagtaatga                                                 20

```
<210> SEQ ID NO 6
<211> LENGTH: 20
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 6
gttaaatgca tcagaagtgt                                               20

<210> SEQ ID NO 7
<211> LENGTH: 20
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 7
taaatgatga caccaggctc                                               20

<210> SEQ ID NO 8
<211> LENGTH: 20
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 8
ctgtccagtt aaatgcatca                                               20

<210> SEQ ID NO 9
<211> LENGTH: 20
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 9
caccaggctc tacagtaatg                                               20

<210> SEQ ID NO 10
<211> LENGTH: 18
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 10
ggaaaggttg gttcgatt                                                 18

<210> SEQ ID NO 11
<211> LENGTH: 19
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 11
ttaaatgatg acaccaggc                                                19
```

```
<210> SEQ ID NO 12
<211> LENGTH: 19
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 12
tggttcgatt ttcagagtc                                             19

<210> SEQ ID NO 13
<211> LENGTH: 19
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 13
gctcaactac gaactccct                                             19

<210> SEQ ID NO 14
<211> LENGTH: 19
<212> TYPE: DNA
<213> ORGANISM: Artificial Sequence
<220> FEATURE:
<223> OTHER INFORMATION: Primers for amplifying different-sized regions
      of the human HTR2A sequence

<400> SEQUENCE: 14
tgagaggcac ccttcacag                                             19

<210> SEQ ID NO 15
<211> LENGTH: 20
<212> TYPE: DNA
<213> ORGANISM: Artificial Sequence
<220> FEATURE:
<223> OTHER INFORMATION: Primers for amplifying regions of certain human
      sequences

<400> SEQUENCE: 15
agatgccaag acaacagata                                            20

<210> SEQ ID NO 16
<211> LENGTH: 18
<212> TYPE: DNA
<213> ORGANISM: Artificial Sequence
<220> FEATURE:
<223> OTHER INFORMATION: Primers for amplifying regions of certain human
      sequences

<400> SEQUENCE: 16
attcactccg tcgctatt                                              18

<210> SEQ ID NO 17
<211> LENGTH: 20
<212> TYPE: DNA
<213> ORGANISM: Artificial Sequence
<220> FEATURE:
<223> OTHER INFORMATION: Primers for amplifying regions of certain human
      sequences

<400> SEQUENCE: 17
ctcatcacca tcgagatcaa                                            20

<210> SEQ ID NO 18
```

```
<211> LENGTH: 20
<212> TYPE: DNA
<213> ORGANISM: Artificial Sequence
<220> FEATURE:
<223> OTHER INFORMATION: Primers for amplifying regions of certain human
      sequences

<400> SEQUENCE: 18
ccaggtctga caacgggtca                                                20

<210> SEQ ID NO 19
<211> LENGTH: 20
<212> TYPE: DNA
<213> ORGANISM: Artificial Sequence
<220> FEATURE:
<223> OTHER INFORMATION: Primers for amplifying regions of certain human
      sequences

<400> SEQUENCE: 19
gtgtgggtgg gagcgcagtg                                                20

<210> SEQ ID NO 20
<211> LENGTH: 19
<212> TYPE: DNA
<213> ORGANISM: Artificial Sequence
<220> FEATURE:
<223> OTHER INFORMATION: Primers for amplifying regions of certain human
      sequences

<400> SEQUENCE: 20 cccaccaaa ggagctgta                                                  19

<210> SEQ ID NO 21
<211> LENGTH: 20
<212> TYPE: DNA
<213> ORGANISM: Artificial Sequence
<220> FEATURE:
<223> OTHER INFORMATION: Primers for amplifying regions of certain human
      sequences

<400> SEQUENCE: 21
ctaacactct tgctcacacc                                                20

<210> SEQ ID NO 22
<211> LENGTH: 20
<212> TYPE: DNA
<213> ORGANISM: Artificial Sequence
<220> FEATURE:
<223> OTHER INFORMATION: Primers for amplifying regions of certain human
      sequences

<400> SEQUENCE: 22
atcctgtgtg gagtgtgtag                                                20

<210> SEQ ID NO 23
<211> LENGTH: 17
<212> TYPE: DNA
<213> ORGANISM: Artificial Sequence
<220> FEATURE:
<223> OTHER INFORMATION: Primers for amplifying regions of certain human
      sequences

<400> SEQUENCE: 23
gccctggtcc acacaag                                                   17

<210> SEQ ID NO 24
<211> LENGTH: 20
```

-continued

```
<212> TYPE: DNA
<213> ORGANISM: Artificial Sequence
<220> FEATURE:
<223> OTHER INFORMATION: Primers for amplifying regions of certain human
      sequences

<400> SEQUENCE: 24
tggtctcatc aaagaagcaa                                              20
```

METHODS FOR DETECTING NUCLEIC ACID SEQUENCE VARIATION

CROSS-REFERENCE TO RELATED APPLICATION

This application claims the benefit of U.S. Provisional Patent Application No. 60/353,941 filed Jan. 31, 2002.

FIELD

The present disclosure relates to methods of detecting sequence variations in nucleic acids, specifically the use of the melting temperature to detect base-pair substitutions, additions, or deletions.

BACKGROUND

Analysis of genetic variation is important in many different applications of molecular biology and medicine, such as mapping nucleic acids, investigating genetic diseases and genetically influenced traits, and assessing the genetic attributes of populations. Assessing this variation depends on the ability to detect polymorphisms, the existence of two or more different alleles of a nucleic acid. Different alleles can be identified according to differences in nucleic acid sequences, and genetic variations occurring in more than 1% of a population (which is the commonly accepted rate of random genetic mutation) are useful polymorphisms for certain applications.

Single nucleotide polymorphisms (SNPs) are an abundant form of nucleic acid sequence variation, occurring at a rate of approximately one per 500 nucleotides in coding sequences, and more abundantly in noncoding sequence. See, e.g., Wang D. G., et al., Science 280:1077-82 (1998). As many as a million SNPs may exist in the human genome.

SNPs of moderate or high abundance (having rare allele frequencies of greater than 10%) are amenable to genotyping using different methodologies, such as DNA arrays (see, e.g., Pastinen, T., et al., Genome Res. 10:1031-42 (2000)), mass spectrometry (see, e.g., Jackson, P. E., et al., Mol. Med. Today 6:271-76 (2000)), and PCR end-plate read methods (see, e.g., Livak, K. J., Genet. Anal. 14:143-49 (1999)). For example, sequencing ten chromosomes (from five persons) will detect approximately two-thirds of all SNPs that have a rare allele frequency of at least 10%. However, SNPs that alter nucleic acid expression or affect structure of the nucleic acid product often have rare allele frequencies of less than 10%. For example, sequencing 10 chromosomes using these known methods will detect less than 10% of SNPs having rare allele frequencies about 1% (which is a frequently used threshold for defining polymorphism). Thus, detecting these rare SNPs with greater efficiency, accuracy, and sensitivity than is now possible would provide a benefit in the investigation of conditions and characteristics related to genetic polymorphisms.

Several methods for SNP detection (such as denaturing gradient gel electrophoresis or denaturing high performance liquid chromatography) are based on the thermodynamic properties of DNA duplexes or single stranded DNA (such as single-strand conformational polymorphism analysis). However, these methods for SNP detection indirectly assess differential melting of heteroduplex DNA, rather than directly detecting such differential melting.

SUMMARY

Disclosed is a method of detecting a nucleic acid sequence variation. Melting profiles of plural nucleic acids are determined and differences between or among the melting profiles indicate a sequence variation between or among nucleic acids.

The sizes of the nucleic acids can be varied, though in some embodiments, the nucleic acids are about 105 bases or longer, such as from about 105 to about 180, or even to about 1000 bases long. Additionally, in some embodiments, the GC content of one (or more) of the nucleic acids is about 70% or less, such as about 50% or less. Both single-stranded and double-stranded nucleic acids can be analyzed, and the double-stranded nucleic acids can be homoduplex or heteroduplex nucleic acids. The nucleic acids can arise from any suitable source, though particular embodiments use mammalian nucleic acids, such as those from a human.

Melting profiles are produced by observing the nucleic acids during a temperature change over a period of time. The rate of temperature change (the melting rate) can be varied, though in certain embodiments, the melting profiles are determined using a melting rate of 0.5° C./minute or less, such as 0.1° C./minute or less, for example, 0.067° C./minute.

Observations of the nucleic acids during the temperature change can be accomplished using a variety of techniques. In particular embodiments, the nucleic acid is contacted with an indicator molecule specific for a double-stranded nucleic acid and the activity of the indicator molecule is detected during the temperature change.

The nucleic acids can be diluted into solutions for analysis. In some embodiments, the nucleic acid concentrations between or among the solutions are substantially the same, such as having a coefficient of variation of less than about 5%, for example, less than about 3%.

The melting profiles and sequence variation can be used to identify changes in a wild-type nucleic acid sequence, such as a single-nucleotide polymorphism (SNP); an insertion or deletion, including small insertions or deletions of one to ten bases; or an inversion, including a small inversion of two to ten bases.

BRIEF DESCRIPTION OF THE DRAWINGS

FIG. 3A illustrates that fluorescence intensity is proportional to dsDNA concentration at varying DNA concentrations of 1 to 6 mg/L and a constant SYBR concentration of 3.6x. The slope of the line is 184, with a y-intercept at 5096 and r=0.99. FIG. 3B illustrates the effect of SYBR dye concentration on dsDNA fluorescence intensity signal. SYBR dye concentration was varied from 1.2x to 18x, with a constant dsDNA concentration of 1.5 mg/L. The slope of the line is −211, with a y-intercept at 8211 and r=0.94. FIG. 3C illustrates the effect of varying SYBR dye concentration (1.8x to 57.6x) on dsDNA melting, as measured by SYBR dye fluorescence intensity.

FIG. 4A is based on chemically synthesized 15-mer oligonucleotides, FIGS. B-D are based on PCR amplicons. In each of FIGS. 4A-D, a heteroduplex/homoduplex mixture (see diagram in FIG. 2) was compared with the homoduplex dsDNA at the same concentration. Derivative melting profiles for homoduplexes are depicted with thick lines, while the melting profile for the heteroduplex/homoduplex mixture is shown with a thin line. Peaks in the melting profiles represent the melting temperature ($T_m$). DNA concentrations were 2 mg/L, and the SYBR dye concentration was 3.6x. Melting curves were acquired at melting rates of 2° C./minute for FIG. 4A, 0.5° C./minute for FIGS. 4B and 4C, and 0.067° C./minute for FIG. 4D.

FIG. 5A illustrates the detection of an SNP in COMT; FIG. 5B illustrates the detection of an SNP in HTR2A C1499T; and FIG. 5C illustrates the detection of a DRD2-141C insertion/deletion. The conditions used for DMA were the same for FIGS. A-C: dsDNA concentration of 2 mg/L; SYBR dye concentration of 3.6x; and a melting rate of 0.067° C./minute. Fluorescence data from melting curves were converted into $T_m$ by plotting the negative derivative of fluorescence versus temperature (−dF/dT vs T). Melting profiles for homozygous DNA are shown with thick lines, while melting profiles for heterozygous DNA are shown by thin lines.

FIG. 6B illustrates the melting domains within the PCR amplicon. The position of the SNP was determined by DNA sequence analysis and is indicated by an arrow.

FIG. 7B illustrates the melting domains within the PCR amplicon. The position of the SNP within the amplicon was determined by DNA sequence analysis and is indicated by an arrow.

In FIG. 8A, the overlapping peaks shown by the arrowhead (G and T) of the determined sequence correspond to nucleotide position 147 of the coding strand of the AChR nucleic acid sequence. In FIG. 8B, the arrowhead indicates two overlapping peaks (A and G) from the noncoding strand of the NR1 nucleic acid sequence.

BRIEF DESCRIPTION OF THE SEQUENCE LISTING

Figure 1:
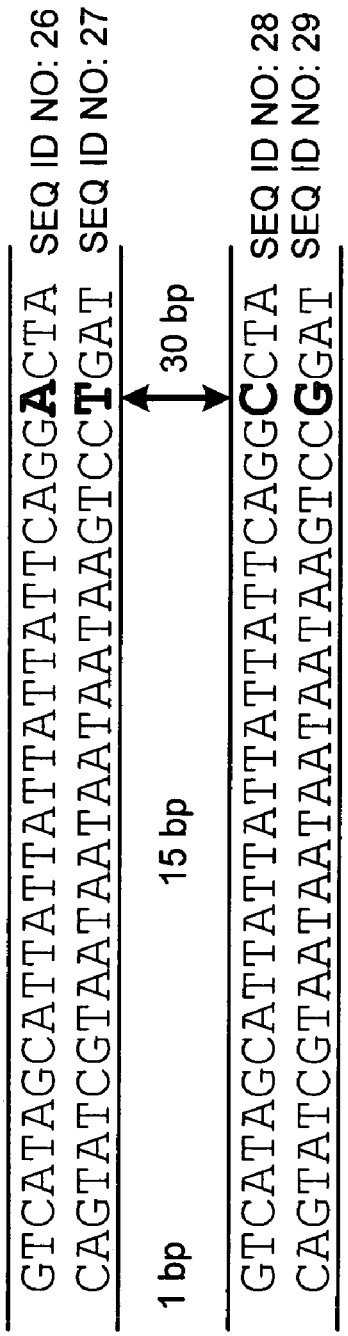
FIGS. 1A-B are schematic diagrams illustrating a single-nucleotide polymorphism (SNP) between a pair of 31 bp dsDNA sequences. The SNP is located at base-pair number 28, where the A-T base-pair of the FIG. 1A dsDNA strand (SEQ ID NOS: 26 and 27) is different than the C-G base-pair of FIG. 1B dsDNA strand (SEQ ID NOS: 28 and 29).

The nucleic acid sequences listed herein are shown using standard letter abbreviations for nucleotide bases. Only one strand of each nucleic acid sequence is shown, but the complementary strand is understood as included by any reference to the displayed strand.

SEQ ID NOS: 1 and 2 show two different 15 bp fragments from the sense strand of human HTR2A containing a polymorphism.

SEQ ID NOS: 3 and 4 show two different 25 bp fragments from the sense strand of human HTR2A containing a polymorphism.

SEQ ID NOS: 5-14 show forward and reverse PCR primers for amplifying fragments of various sizes from human HTR2A.

SEQ ID NOS: 15-24 show forward and reverse PCR primers for amplifying fragments of the human HTR2A, COMT, DRD2, NR1, and AChR nucleic acids.

SEQ ID NO: 25 is the complement of SEQ ID NO: 5.

SEQ ID NOS: 26-27 are nucleic acid sequences that form a ds DNA molecule.

SEQ ID NOS: 28-29 are nucleic acid sequences that form a ds DNA molecule.

SEQ ID NOS: 30-31 are nucleic acid sequences used to show the meaning of the term complementary.

DETAILED DESCRIPTION

I. Abbreviations
A=adenine
AChR=human acetylcholine receptor α-subunit nucleic acid
C=cytosine
COMT=Catechol-O-methyltransferase nucleic acid
dHPLC=denaturing high-performance liquid chromatography
−dF/dT=negative derivative of fluorescence
dGGE=denaturing gradient gel electrophoresis
DMA=DNA melting analysis
DNA=deoxyribonucleic acid
ds=double-stranded (for example, dsDNA)
G=guanine
HTR2A=hydroxytryptamine receptor 2A nucleic acid
mg=milligram
ng=nanogram
NR1=N-methyl-D-aspartate receptor subunit 1 nucleic acid
PCR=polymerase chain reaction Pu=purine
Py=pyrimidine
RNA=ribonucleic acid
SNP=single-nucleotide polymorphism
ss=single-stranded (for example, ssDNA)
SSCP=single-strand conformational polymorphism analysis
SYBR=SYBR Green I
T=thymine
$T_m$=melting tempature
U=uracil II. Terms and Explanations The following explanations of terms are provided in order to facilitate review of the embodiments described herein. Explanations of common terms also can be found in Rieger et al., *Glossary of Genetics: Classical and Molecular*, 5th edition, Springer-Verlag: New York, 1991; Lewin, *Nucleic acids VII*, Oxford University Press: New York, 1999; and *Dictionary of Bioscience*, Mcgraw-Hill: New York, 1997.

The singular forms "a," "an," and "the" refer to one or more than one, unless the context clearly dictates otherwise. For example, the term "comprising a nucleic acid" includes single or plural nucleic acids and is considered equivalent to the phrase "comprising at least one nucleic acid."

The term "or" refers to a single element of stated alternative elements or a combination of two or more elements. For example, the phrase "a first nucleic acid or a second nucleic acid" refers to the first nucleic acid, the second nucleic acid, or a combination of both the first and second nucleic acids.

As used herein, "comprises" means "includes." Thus, "comprising A and B" means "including A and B," without excluding additional elements.

Amplification of a nucleic acid. Any of several techniques that increases the number of copies of a nucleic acid molecule. An example of amplification is the polymerase chain reaction (PCR), in which a sample containing the nucleic acid is contacted with a pair of oligonucleotide primers under conditions that allow for the hybridization of the primers to nucleic acid in the sample. The primers are extended under suitable conditions, dissociated from the template, and then re-annealed, extended, and dissociated to amplify the number of copies of the nucleic acid. The amplification products (called "amplicons") can be further processed, manipulated, or characterized by (without limitation) electrophoresis, restriction endonuclease digestion, hybridization, nucleic acid sequencing, ligation, or other techniques of molecular biology. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in European Patent Appl. 320 308; gap filling ligase chain reaction amplification, as disclosed in U.S. Pat. No. 5,427,930; and NASBA™ RNA transcription-free amplification, as disclosed in U.S. Pat. No. 6,025,134.

Animal. A living, multi-cellular, vertebrate organism, including, for example, mammals, birds, reptiles, and fish. The term "mammal" includes both human and non-human mammals.

Complementary. Regarding nucleic acids, complementary binding occurs when the base of one nucleic acid molecule forms a hydrogen bond the base of another nucleic acid molecule. Normally, the base adenine (A) is complementary to thymidine (T) and uracil (U), while cytosine (C) is complementary to guanine (G). For example, the sequence 5'-ATCG-3'(SEQ ID NO: 30) of one ssDNA molecule can bond to 3'-TAGC-5' (SEQ ID NO: 31) of another ssDNA to form a dsDNA.

Nucleic acid molecules can be complementary to each other even without complete hydrogen-bonding of all bases of each molecule. For example (and without limitation), the ssDNA
   5'-ACCAGGCTCTACAGTAATGA-3' (SEQ ID NO: 5)
is considered complementary to the ssDNA
   3'-TGGTTCGAGATGTCATTACT-5' (SEQ ID NO: 25)
even though there is a mismatched base pair (G-T rather than G-C or A-T) at the fifth position.

GC content. Refers to the relative number of G or C bases within a nucleic acid. For example, a ssDNA that is 200 bp in length with 120 bases being G or C would have a GC content of 60%, while a homoduplex dsDNA that is 250 bp in length with 100 bases of the coding strand being G or C would have a GC content of 40%.

Genetic disease. A disease that has its origin in changes to the genetic material, such as DNA. Some genetic diseases are inherited in a Medelian fashion, for example, a disease arising in a double-recessive homozygote. Noninherited genetic diseases, such as certain neoplastic diseases, can arise as the result of mutation.

Exemplary genetic diseases include (but are not limited to) sickle cell anemia, diabetes, Alzheimer's disease, Huntington's disease, certain types of breast cancer (resulting from mutations to BRC A1 or BRC A2, for example), and retinoblastoma. Particular genetic diseases resulting from SNPs include (but are not limited to) cystic fibrosis, sickle cell anemia, Factor VIII hemophilia (from a mutation in FC8), Duchenne/Becker muscular dystrophy (D/BMD), Type 1 von Willebrand disease, familial Alzheimer's disease, familial hypercholesterolaemia (FH), and diseases resulting from a mutation in nucleic acid encoding the low-density lipoprotein (LDL) receptor.

Heteroduplex. A "heteroduplex" nucleic acid is a double-stranded nucleic acid where the two strands are not fully complementary. For example (and without limitation), a heteroduplex DNA can be formed from a pair of DNA sequences having a single base-pair mismatch along the duplexed molecules, such as an A-C mismatch instead of the matched (complementary) A-T base pairing.

In some embodiments, heteroduplex DNA molecules are formed after denaturing a heterozygous genomic sequence when different allelic strands hybridize and anneal to one another. As one specific, non-limiting example, heteroduplex dsDNAs could be formed when the heterozygous sequences illustrated in FIGS. 1A-B are denatured and the top strand of FIG. 1A hybridizes with the bottom strand of FIG. 1B, thus inducing an A-G mismatch based on the illustrated SNP.

Homoduplex. A "homoduplex" nucleic acid is a double-stranded nucleic acid where the two strands are fully complementary.

Hybridization. Hybridization of a nucleic acid occurs when two complementary nucleic acid molecules undergo at least some degree of hydrogen bonding to each other. The stringency of hybridization can vary according to the environmental conditions surrounding the nucleic acids, the nature of the chosen hybridization method, and the composition and length of the nucleic acids used. Temperature and ionic strength (for example, the Na$^+$ concentration) can affect the stringency of hybridization. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001).

By way of illustration only, hybridization can occur by melting and reannealing a double-stranded nucleic acid, such as a dsDNA. The term $T_m$ represents the temperature at which 50% of a given strand of nucleic acid is hybridized to its complementary strand.

The $T_m$ of a particular nucleic acid can be determined by observing the transition state between a single-stranded and double-stranded state during a temperature change, such as heating a dsDNA from about 30° C. to about 100° C., and detecting when the dsDNA denatures to ssDNA. This can be accomplished by determining a melting profile for the nucleic acid.

Additionally, a $T_m$ an immobilized nucleic acid can be determined according to following equation:

$$T_m = 81.5\ C - 16.6(\log_{10}[Na^+]) + 0.41(\%\ G+C) - 0.63(\%\ \text{formamide}) - (600/l)$$

Where l=the length of the hybrid in base pairs.

This equation is valid for concentrations of $Na^+$ in the range of 0.01 M to 0.4 M, and it is less accurate for calculations of $T_m$ in solutions of higher $[Na^+]$. The equation is also primarily valid for nucleic acids whose GC content is in the range of 30% to 75% and whose length is about 100 nucleotides or greater.

For oligonucleotides of about 20 bases, the classical formula for $T_m$ is: $T_m = 2 \times (A+T) + 4 \times (G+C)$.

For longer nucleic acid fragments, such as PCR products, the nearest-neighbor method can be used to determine $T_m$. See, e.g., Breslauer K. J., et al., Proc. Natl. Acad. Sci. USA 83:3746-50 (1986). Additionally, the MeltCalc software can be used to determine $T_m$. See, e.g., Schütz, E. and von Ahsen, N., Biotechniques 30:8018-22, 24 (1999).

The $T_m$ of dsDNA decreases by about 1.0 to 1.5° C. with every about 1% decrease in sequence homology. For example, a heteroduplex dsDNA of about 100 bp with an SNP has a $T_m$ about 1.0 to 1.5° C. lower than a corresponding homoduplex dsDNA.

Isolated. An "isolated" biological component (such as a nucleic acid, polypeptide, protein, or bacteriophage) has been substantially separated, produced apart from, or purified away from other biological components (for example, other chromosomal and extrachromosomal DNA and RNA, polypeptides, or lipids). Nucleic acids, polypeptides and proteins that have been "isolated" can, for example, have been purified by standard purification methods. The term also embraces nucleic acids, polypeptides, and proteins that are chemically synthesized or prepared by recombinant expression in a host cell. Exemplary methods of synthesis and purification can be found in Sambrook, et al. (2001).

Melting profile. A melting profile is composed of data obtained during an analysis of melting and reannealing of a nucleic acid. The double-stranded or single-stranded state of the nucleic acid is monitored as the surrounding temperature is changed, for example, by raising the temperature of a solution containing a dsDNA and detecting the transition from a dsDNA to a ssDNA.

The rate of temperature change used in a nucleic acid melting analysis can be progressively decreased as the length of the nucleic acid increases. In some embodiments, for example, the melting profile for a 25 bp nucleic acid is determined using about a 2° C./minute temperature change, while the melting profiles for nucleic acids of 100 bp or longer are determined using a rate of temperature change of about 0.5° C./minute or less, such as 0.1° C./minute or less. In particular embodiments, the rate of temperature change is about 0.067° C./minute.

A melting profile can be determined for any nucleic acid. In certain embodiments, the nucleic acid is a double-stranded nucleic acid, such as dsDNA, dsRNA, or a dsDNA/RNA hybrid. The data of a melting profile can be graphically represented, for example, as illustrated in FIGS. 4-7.

Nucleic acid. A nucleotide (deoxyribonucleotide or ribonucleotide) polymer, in either single or double stranded form, that forms a nucleic acid sequence. A single nucleotide (or "base") is a molecule a comprising a sugar (ribose or deoxyribose) linked to a phosphate group and to an exchangeable organic base. Exemplary non-limiting organic bases include (but are not limited to) a substituted or substituted pyrimidine (Py) or purine (Pu). Exemplary non-limiting pyrimidines include cytosine (C), thymine (T), and uracil (U)), while exemplary non-limiting purines include adenine (A) or guanine (G). Particular nucleic acids disclosed herein are double-stranded DNA molecules.

Oligonucleotide. Multiple nucleotides linked together. The term "oligonucleotide" refers to both oligoribonucleotides (ORNs) and oligodeoxyribonucleotides (ODNs). The term "oligonucleotide" also includes oligonucleosides (an oligonucleotide minus the phosphate groups) and any other organic base polymer. Oligonucleotides can be obtained from existing nucleic acid sources (such as genomic DNA or cDNA) or can be synthesized.

Polymorphism. Polymorphism exists when two or more versions of a nucleic acid sequence exist within a population of subjects. For example (and without limitation), a polymorphic nucleic acid is one for which the most common allele has a frequence of 99% or less. Different alleles can be identified according to differences in nucleic acid sequences, and genetic variations occurring in more than 1% of a population (which is the commonly accepted frequency for defining polymorphism) are useful polymorphisms for certain applications.

The allelic frequency (the proportion of all allele nucleic acids within a population that are of a specified type) can be determined by directly counting or estimating the number and type of alleles within a population. Polymorphisms and methods of determining allelic frequencies are discussed in Hartl, D. L. and Clark, A. G., Principles of Population Genetics, Third Edition (Sinauer Associates, Inc., Sunderland Mass., 1997), particularly in chapters 1 and 2.

Purified. The term "purified" does not require absolute purity; rather, it is intended as a relative term. A purified molecule is one in which the molecule is more enriched than it is in its natural environment, such as a preparation in which the molecule represents at least 50% of the total content of similar molecules within the sample. For example, a purified solution of NR1 nucleic acid is one in which NR1 represents at least 50% of all nucleic acids within the sample, for example, at least 75%, at least 90%, at least 95%, or at least 99%.

Single nucleotide polymorphism (SNP). A nucleic acid sequence variation that results from a change in a single nucleotide in a genomic sequence. A SNP can occur in a coding or non-coding regions of a genome, and a SNP in a coding region optionally can generate a polymorphic variant of an expressed amino acid having a different functional property.

Exemplary non-limiting mutations leading to SNPs include transitions and transversions. A transition is the replacement of one purine by another purine or of one pyrimidine by another pyrimidine. A transversion is the replacement of a purine by a pyrimidine or of a pyrimidine by a purine.

Subject. The term "subject" includes any organism or entity from which a nucleic acid can be extracted, such as humans, non-human animals, plants, fungi, and microorganisms. Representative microorganisms include (but are not limited to) bacteria and other microscopic prokaryotes, amoeba and other microscopic eukaryotes, and viruses.

Substantially the same concentration. The similarity of concentrations of a substance within multiple solutions can be measured by determining a coefficient of variation for the concentration of that substance. Solutions demonstrating a coefficient of variation of about 5% or less for the concentration of a substance are considered to have substantially the same concentration of that substance. In particular embodiments, the coefficient of variation is less than 5%, such as less than about 3%, for example within a range of about 0.5% to about 3%.

In certain non-limiting embodiments, solutions are considered to have substantially the same nucleic acid concentration or dye concentration if the coefficient of variation is about 3% or less for the concentration of that nucleic acid or dye. The coefficient of variation (CV) is the standard deviation for a variable divided by the mean value of the variable. CV values can be expressed as a percentage.

Wild-type. The genotype or phenotype that is most prevalent in nature. The naturally occurring, non-mutated version of a nucleic acid sequence. Among multiple alleles, the allele with the greatest frequency within the population is usually (but not necessarily) the wild-type. The term "native" can be used as a synonym for "wild-type."

III. Detecting Sequence Variation Based on Melting Profiles

A method is disclosed for detecting a nucleic acid sequence variation based on differences in melting profiles for plural nucleic acids. For example, the melting profile for a first nucleic acid, such as a native nucleic acid, can be compared to the melting profile for a second nucleic acid, such as a mutant nucleic acid. However, more than two nucleic acids can be used and sequence variation can be detected by comparison to the melting profiles of several nucleic acids, such as a collection of wild-type and mutant sequences. In some embodiments, the melting profiles are determined simultaneously by analyzing the nucleic acids during a temperature change over time. In other embodiments, however, a melting profile is determined for a single nucleic acid and compared to a reference standard melting profile, such as one previously determined or obtained from another source. Sequence variation is detected based on differences in melting profiles, such as differences in $T_m$.

The nucleic acids analyzed can be single- or double-stranded, though certain embodiments employ double-stranded nucleic acids, such as dsDNA molecules. The method is not limited to detection sequence variability between or among dsDNA molecules, however. For example (and without limitation), sequence variations in single-stranded mRNA molecules can be analyzed by using complementary RNA or DNA molecules to determine the melting profiles of the mRNAs based on the corresponding dsRNA or dsRNA/DNA hybrid molecules.

The nucleic acids can be obtained from any suitable source and can be of any type, such as being isolated from a subject or obtained from another party that has isolated the nucleic acid. The size of the nucleic acid analyzed also can vary. In some embodiments, the nucleic acid is at least 105 nucleotides in length, such as a dsDNA of 105 bp or longer.

In alternative embodiments, the nucleic acid is about 1000 bp or less, such as a nucleic acid that is about 750 bp or less, about 500 bp or less, about 250 bp or less, or about 150 bp or less. In specific embodiments, the nucleic acid has a length of about 105 bp to about 1000 bp.

Additionally, a nucleic acid can be selected according to a particular characteristic. For example, genomic sequences located near markers for genetic disease can be analyzed to detect sequence variation among wild-type and mutant forms, or a nucleic acid can be selected based on nucleotide composition. In contrast to methods that employ nucleic acids having GC-clamps (see, e.g., Elenitoba-Johnson and Bohling, Am. J. Pathology 159(3):845-53 (2001)), some disclosed embodiments employ nucleic acids having a low GC content, such as a GC content of about 70% or less, such as about 50% or less. Other embodiments employ nucleic acids having a GC content of about 40% to about 70%.

Double-stranded nucleic acids can be either homoduplex or heteroduplex nucleic acids. In some embodiments, at least one nucleic acid is a homoduplex and another is a heteroduplex, thus creating different melting profiles. Additionally, the nucleic acids can be processed or manipulated in some manner, such as being amplified, digested by restriction endonucleases, or labeled.

In some embodiments, the nucleic acids are diluted in one or more solutions, arranged in an array, and/or placed on a solid substrate (for example, a DNA microchip). In certain embodiments, the nucleic acids are diluted in an organic or inorganic solvent to form solutions. The solution optionally can contain additives, such as stabilizers, preservatives, or buffers. In particular embodiments, a dye—such as a fluorescent dye—is added to the solution to assist in determining the transition of the nucleic acid between single- and double-stranded states.

The nucleic acid concentration of a solution can vary. In some embodiments, the nucleic acids are diluted in solutions to provide substantially the same nucleic acid concentration in each solution. Solutions having substantially the same nucleic acid concentration can be achieved using a variety of techniques, such as accurately measuring the amount of nucleic acid contained within each sample volume. For example, the concentration of a dsDNA in solution can be accurately measured by adding a dsDNA specific fluorescent dye to the solution and detecting the initial fluorescence intensity using a fluorometer. Additionally, a certain nucleic acid concentration can be achieved using consistent amplification conditions, such as described in the Examples below. In some embodiments, the nucleic acid concentration is from about 0.1 mg/L to about 10 mg/L, such as from about 0.5 mg/L to about 5 mg/L, or from about 0.8 mg/L to about 4 mg/l, such as about 2.0 mg/L.

The melting profile of the nucleic acid is determined by analyzing the transition of the nucleic acid between single-stranded and double-stranded states. For example, a double-stranded nucleic acid can be heated to denature and form single-stranded nucleic acids, or a single-stranded nucleic acid in the presence of a complementary strand can be cooled to induce hybridization and annealing, thus forming a double-stranded molecule.

Determining whether a nucleic acid exists in a single- or double-stranded state can be accomplished using a variety of techniques. In certain embodiments, the nucleic acid is contacted with an indicator molecule specific for the double-stranded state and the intensity or activity of the indicator is measured. Exemplary indicators include dsDNA-specific dyes such as ethidium bromide, YO-PRO-1 dye, Hoechst 33258 dye, Pico Green dye, and SYBR Green I dye. In alternative embodiments, the single- or double-stranded state of the nucleic acid is determined by ultraviolet (UV) absorbency, nuclear magnetic resonance, circular dichroism, changes in volume of a sample or solution containing the nucleic acid, resonance energy transfer, or optical wave guides (such as in a nucleic acid microarray). While other alternative embodiments use oligonucleotide probes to detect a single- or double-stranded state, the use of such probes is not necessary.

In some embodiments, the melting profile of a double-stranded nucleic acid, such as a genomic dsDNA sequence, is determined by heating that nucleic acid and detecting whether the nucleic acid has remained double-stranded at a particular temperature or has denatured into single strands. Alternatively, the melting profile of a single-stranded nucleic acid, such as a single-stranded mRNA sequence, is determined by placing that nucleic acid in the presence of a complementary nucleic acid (its complement) and detecting whether the single-stranded nucleic acid exists in a single-stranded form or has hybridized and annealed with its complement to form a double-stranded nucleic acid at a known temperature.

A melting profile is established by correlating the temperature of the nucleic acid or its surrounding environment with the single- or double-stranded state of the nucleic acid. For example (and without limitation), as illustrated in FIGS. 3-6 and described in further detail in the Examples below, this data can be graphically represented by plotting the temperature against the fluorescence activity of an indicator molecule specific, for dsDNA. As the temperature increases (from left to right in the graphs of FIGS. 3-6), the proportion of dsDNA within the sample decreases, indicating that the dsDNA molecules are begining to denature and separate into single strands. In FIGS. 3A-D, 4A-C, 5A, and 6A, the data for indicator activity was converted into melting peaks ($T_m$) for the DNA by plotting the negative derivative of indicator activity (fluorescence) versus temperature (−dF/dT vs T).

The rate of temperature change used to determine a melting profile (also called the "melting rate") can be varied. As described above, the melting profiles for shorter nucleic acids can employ a higher rate of temperature change than the melting profiles for longer nucleic acids. In some embodiments, the rate of temperature change is about 5° C./minute or less, such as about 2° C./minute or less, or even less than 1° C./minute. In particular embodiments, the rate of temperature change is about 0.067° C./minute, though still lower rates of temperature change can be used, such as about 0.05° C./minute or less.

A difference between or among melting profiles indicates sequence variation between or among the corresponding nucleic acids. In some embodiments, the sequence variation detected is an SNP, an insertion, a deletion, or an inversion. In particular embodiments, a small insertion, small deletion, or small inversion is detected based on the melting profile, such as an insertion, deletion, or inversion of nucleotides equal to less than about 5% of the total nucleic acid sequence, for example, less than about 3% of the total nucleic acid sequence, less than about 2% of the total nucleic acid sequence, or even less than about 1% of the total nucleic acid sequence. In other embodiments, the small insertion, small deletion, or small inversion is about 10 nucleotides or less, such as about 5 nucleotides or less, or even 2 or 1 nucleotides.

Prior knowledge about the existence of any variation among the sequences is not necessary. In fact, determining melting profiles and detecting differences between or among the corresponding nucleic acids can be accomplished without any prior knowledge about the existence of any variant sequence, such as an SNP, small insertion, small deletion, or small inversion.

Information about sequence variation can be used in a variety of ways. For example, polymorphisms—even SNPs—can be used to assess allelic frequencies within populations, construct genetic maps, or identify genetic diseases. Melting profiles and the resulting sequence variation information can be useful for studying molecular interactions and signal transduction systems, such as nucleic acid interactions with hormones, repressors, transcription factors, chromatin, and other cellular molecules; in vitro molecular mechanisms, such as RNA splicing or post-transcriptional modification; and for studying the role of modified bases in nucleic acid chemistry, such as for drug design and development of anti-viral agents.

In some embodiments, a genetic disease in a subject is detected based on a difference between the melting profiles of a nucleic acid obtained from that subject and the corresponding wild-type nucleic acid. In particular embodiments, the genetic disease results from an SNP.

An array containing a plurality nucleic acids can be used to rapidly identify sequence variation between or among the nucleic acids. In such embodiments, a melting profile is determined for each of the nucleic acids within the array and the profiles are compared to assess the correlated sequence variation.

Arrays are arrangements of addressable locations on a substrate, with each address containing a nucleic acid. In some embodiments, each address corresponds to a single type or class of nucleic acid, such as a single dsDNA, though a particular nucleic acid can be redundantly contained at multiple addresses.

A "microarray" is a miniaturized array requiring microscopic examination for determination of the melting profile. Larger "macroarrays" allow each address to be recognizable by the naked human eye and, in some embodiments, are detectable without additional magnification. For example, if an indicator specific for double-stranded nucleic acids is used (for example, SYBR Green I dye), detection of the single- or double-stranded state of the nucleic acid can be accomplished by detecting the indicator signal (for example, fluorescence) within the array addresses.

In some embodiments, a nucleic acid array is a collection of dsDNA molecules at the array addresses. As one, non-limiting example, the array can contain human genomic sequences. This system permits the simultaneous analysis of a multiple DNA sequences by determining the melting profiles for the DNA sequences within the array and assessing the resulting variability for that population of DNA sequences. In alternative embodiments, the array contains ssRNA molecules and their complementary RNA (or DNA) strands.

The nucleic acids can be added to an array substrate in dry or liquid form. Other compounds or substances can be added to the array as well, such as buffers, stabilizers, reagents for detecting indicator signals, emulsifying agents, or preservatives.

Within an array, each arrayed nucleic acid is addressable—its location can be reliably and consistently determined within the at least the two dimensions of the array surface. Thus, ordered arrays allow assignment of the location of each nucleic acid at the time it is placed within the array. The addresses can be labeled, keyed to a separate guide, or otherwise identified by location. Usually, an array map or key is provided to correlate each address with the appropriate nucleic acid. Ordered arrays are often arranged in a symmetrical grid pattern, but the array addresses could be arranged in other patterns (for example, in radially distributed lines, a "spokes and wheel" pattern, or ordered clusters).

An address within the array can be of any suitable shape and size. In some embodiments, the addresses are square or rectangular wells on the array substrate. However, other addresses can be essentially triangular, oval, circular, or irregular. The overall shape of the array itself also can vary, though in some embodiments it is substantially flat and rectangular or square in shape.

Nucleic acid arrays can vary in structure, composition, and intended functionality, and can be based on either a macroarray or a microarray format, or a combination thereof. Such arrays can include, for example, at least 10, at least 25, at least 50, at least 100, or more addresses, usually with a single type of nucleic acid at each address. In the case of macroarrays, sophisticated equipment may not be required to determine the melting profiles, though quantification can be assisted by standard scanning and/or quantification techniques and equipment. Thus, macroarray analysis as described herein can be carried outwithout the need for investment in specialized and expensive reading equipment.

Examples of substrates for the arrays disclosed herein include glass (for example, functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example, glass or a supported membrane) or flexible (such as a polymer membrane). One commercially available product line suitable for probe arrays described herein is the Microlite line of Microtiter® plates available from Dynex Technologies UK (Middlesex, United Kingdom), such as the Microlite 1+ 96-well plate, or the 384 Microlite+ 384-well plate.

Addresses on the array should be discrete, in that individual addresses can be distinguished from neighboring addresses, either by the naked eye (macroarrays) or by scanning or reading by a piece of equipment or with the assistance of a microscope (microarrays).

Addresses in an array can be of a relatively large size, such as large enough to see without the assistance of a microscope or other equipment. Thus, addresses can be as small as about 0.1 mm across, with a separation of about the same distance. Alternatively, addresses can be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (for example, larger addresses will usually be found on larger arrays, while smaller addresses can be found on smaller arrays). Such a correlation is not necessary, however.

The arrays herein can be described by their densities—the number of addresses in a certain specified surface area. For macroarrays, array density can be about one address per square decimeter (or one address in a 10 cm by 10 cm region of the array substrate) to about 50 addresses per square centimeter (50 addresses within a 1 cm by 1 cm region of the substrate). For microarrays, array density usually will be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the nucleic acids could be contained on a DNA microchip similar to the GeneChip® products and related products commercially available from Affymetrix, Inc. (Santa Clara, Calif.). Briefly, a DNA microchip is a miniaturized, high-density array of nucleic acids on a glass wafer substrate. Particular nucleic acids are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for use.

In one exemplary embodiment, multiple double-stranded nucleic acids are diluted into solutions and distributed into separate wells of a multi-well plate (alternatively, the solutions could be distributed into a collection of containers). A different nucleic acid can be placed in each well, or aliquots of the nucleic acid could be placed in multiple wells for redundancy purposes. Aliquots of an indicator molecule specific for double-stranded nucleic acids (for example, a fluorescent dye) are then added to the wells. The wells are then heated according to a set melting rate and the indicator activity of each well is detected at certain temperatures over time. This data is then collected and used to develop melting profiles for the nucleic acids.

In other exemplary embodiments, the method is automated using equipment that permits simultaneous analysis of a large number of samples, such as 96 samples in a 96-well plate.

EXAMPLES

The following examples are provided to illustrate particular features of certain embodiments, but the scope of the claims should not be limited to those features exemplified.

Summary of Examples dsDNA melting was controlled and monitored in a 96-well plate assay using the dsDNA specific fluorescent dye, SYBR Green I (SYBR) dye, and a PE 7700 Sequence-Detector, which allowed the simultaneous DNA melting and fluorescence quantitation in a 96-well format. The decrease in fluorescence intensity that accompanied DNA duplex denaturation was measured. Effects of fragment length, dye concentration, DNA concentration, and sequence context were assessed using four naturally occurring polymorphisms —three SNPs and a single-base deletion/insertion. Additionally, two previously unknown SNPs were discovered.

DNA melting analysis (DMA) was successfully used for sequence variant detection. DNA concentration was found to affect heteroduplex detection by DMA, though amplicon concentrations were readily monitored by SYBR fluorescence and were highly reproducible, with a coefficient of variation of 2.6%.

Significant differences in $T_m$ were detected among homoduplex and heteroduplex fragments 15 bp to 167 bp in length and differing by only a single nucleotide substitution. The efficiency and sensitivity of this DMA makes it suitable and efficient for large-scale detection of sequence variants.

Example 1

Melting Profiles

Oligonucleotide Synthesis

An ABI 394 DNA/RNA Synthesizer (Perkin Elmer, Foster City, Calif.) was used to synthesize the oligonucleotides used to create the 15 bp and 25 bp HTR2A fragments. Four oligomers were synthesized with the variant nucleotide at position 8 of the 15 bp fragment and position 13 of the 25 bp fragment. The two sense strands contained either a T or C. The two complementary strands contained either an A or G. The ssDNAs were annealed to create pure homoduplexes (perfect match) or pure heteroduplex molecules (single base mismatch). To test the ability to detect a single base mismatch in a dsDNA mixture composed of both homoduplexes and heteroduplexes, the heteroduplex DNA was diluted with homoduplex DNA in a 1:1 molar ratio.

The sequences of the fragments were:

```
(HTR2A 15 bp): 5'-TTAACTCT/CGGAGAAG-3'          (SEQ ID NOS: 1 and 2)
and (HTR2A 25 bp): 5'-TGACTTTAACTCT/CGGAGAAGCTAAC-3'  (SEQ ID NOS: 3-4)
Mismatches are underlined.
```

PCR Amplification of Human Genomic DNA.

DNA fragments of 60 bp or greater were synthesized by PCR on human genomic DNA templates. In the case of known SNPs, such as the HTR2A 102T→C, DNA sequences were selected from subjects that were either homozygous (HTR2A 102T→C 102T/102T) or heterozygous (HTR2A 102T→C HTR2A 102T/102C) for an allele.

The total volume for the PCR reaction was 25 μl and contained: 100 ng genomic DNA; 0.25 mM dNTPs; 0.5 μM PCR primers; and 0.75 units of AmpliTaq Gold with appropriate buffer (Perkin Elmer). PCR master mixes were prepared daily. The denaturation and extension steps for all PCRs were at 95° C. for 15 s and at 72° C. for 30 s in 30 cycles. The annealing temperature for the 60, 78, 100, or the 152 bp amplicons was 50° C. for 20 s. Each fragment was amplified using the following primers:

```
60bp
Forward:
5'-ACCAGGCTCTACAGTAATGA-3'   (SEQ ID NO: 5)

Reverse:
5'-GTTAAATGCATCAGAAGTGT-3'   (SEQ ID NO: 6)

78bp
Forward:
5'-TAAATGATGACACCAGGCTC-3'   (SEQ ID NO: 7)

Reverse:
5'-CTGTCCAGTTAAATGCATCA-3'   (SEQ ID NO: 8)

97bp
Forward:
5'-CACCAGGCTCTACAGTAATG-3'   (SEQ ID NO: 9)

Reverse:
5'-GGAAAGGTTGGTTCGATT-3'     (SEQ ID NO: 10)

100bp
Forward:
5'-TTAAATGATGACACCAGGC-3'    (SEQ ID NO: 11)

Reverse:
5'-TGGTTCGATTTTCAGAGTC-3'    (SEQ ID NO: 12)

152bp
Forward:
5'-GCTCAACTACGAACTCCCT-3'    (SEQ ID NO: 13)

Reverse:
5'-TGAGAGGCACCCTTCACAG-3'    (SEQ ID NO: 14)
```

For other known SNPs, the annealing step for the variants tested was 20 s. Annealing temperatures were: 55° C., for HTR2A His452Tyr; 54° C. for COMT Val158Met; and 59° C. for DRD2-141 Ins/Del. For screening unknown SNPs, the annealing step was performed at 60° C. for 20 s.

PCR amplicons used for SNP screening by DMA were based on exon sequences of the NMDA receptor nucleic acid (NR1, Genbank accession Z32773) and both exon and intron sequences from the acetylcholine receptor nucleic acid (AChR) α-subunit (Genbank accession X02502). The primer sequences used to amplify these sequences were:

```
HTR2A:
Forward: 5'-AGATGCCAAGACAACAGATA-3'  (SEQ ID NO: 15)

Reverse: 5'-ATTCACTCCGTCGCTATT-3'    (SEQ ID NO: 16)

COMT:
Forward: 5'-CTCATCACCATCGAGATCAA-3'  (SEQ ID NO: 17)

Reverse: 5'-CCAGGTCTGACAACGGGTCA-3'  (SEQ ID NO: 18)

DRD2:
Forward: 5'-GTGTGGGTGGGAGCGCAGTG-3'  (SEQ ID NO: 19)

Reverse: 5'-CCCCACCAAAGGAGCTGTA-3'   (SEQ ID NO: 20)

NR1:
Forward: 5'-CTAACACTCTTGCTCACACC-3'  (SEQ ID NO: 21)

Reverse: 5'-ATCCTGTGTGGAGTGTGTAG-3'  (SEQ ID NO: 22)

AChR:
Forward: 5'-GCCCTGGTCCACACAAG-3'     (SEQ ID NO: 23)

Reverse: 5'-TGGTCTCATCAAAGAAGCAA-3'  (SEQ ID NO: 24)
```

Following PCR amplification, each product was purified using either the Qiagen (Santa Clarita, Calif.) kit for PCR, or gel extraction. The purified product was then denatured at 95° C. for 4 min and re-annealed by slowly cooling to 60° C. over a period of 30 min in order to permit the formation of a mixture of homoduplex and heteroduplex molecules in the DNA amplified from heterozygous subjects.

SYBR Fluorescence Detection of DNA Melting.

SYBR Green I (SYBR) dye used for DMA, is a proprietary dye specific for double-strand nucleic acids and was obtained from Molecular Probes (Eugene, Oreg.). Both the structure and concentration of SYBR dye are proprietary, and SYBR dye is reported to bind to the minor groove of dsDNA (Molecular Probes Manual, Eugene, Oreg.). The optimal excitation and emission spectra of SYBR dye are centered at 492 nm and 513 nm, respectively. SYBR dye is supplied as a 10,000× concentrate by the manufacturer (Molecular Probes, Eugene, Oreg.) with no molar concentration values or formula weights being supplied.

The optimal concentration of SYBR dye used in our experiments was determined to be 3.6× dye (reduced from 10,000×) and dilutions were with 1× TBE buffer. The 3.6× SYBR dye concentration was useful for concentrations of DNA between 20 and 100 ng in 15 μl. Fluorescence measurements and denaturation were accomplished using the PE 7700 Sequence detector (Perkin Elmer, Foster City, Calif.). Fluorescence signals were recorded approximately every seven seconds over the entire time course of denaturation, which varied from 30 min to 4 hr, gathering data for up to 96 samples at a time.

Data Analysis.

Following DNA duplex denaturation and data acquisition, raw fluorescence data was exported to a Microsoft Excel® spread sheet for statistical analyses. Fluorescence data from melting curves were converted into melting peaks ($T_m$) by plotting the negative derivative of fluorescence versus temperature (−dF/dT vs T). Melting point predictions were performed using MeltCalc software. Schütz, E. and von Ahsen, N., Biotechniques 30:8018-22, 24 (1999).

Variant Screening Using dHPLC

Following PCR amplification, samples were denatured and re-annealed as described above for DMA analysis to enhance formation of DNA heteroduplexes. Samples were then processed using a denaturing high performance liquid chromatography (d HPLC) system, consisting of a 96-well autosampler, column oven, pumps, degasser, variable wavelength UV detector, sample loop, and a PC-based data collection system obtained from Transgenomic Inc. (Omaha, Nebr.). Prior to dHPLC, melting curves for PCR amplicons were simulated using the Transgenomic Wavemaker™ software to determine if any significant shifts in $T_m$ could be predicted for the amplicon. A Transgenomic DNASep column was used for separations. Buffers used on the column were:

Buffer A—10 mM tri-ethyl ammonium acetate (TEAA, pH 7.4); and

Buffer B—10 mM TEAA plus 25% acetonitrile.

Loading buffer consisted of 8% acetonitrile. Melting temperatures and buffer gradients were determined using the Transgenomic melting temperature predictions software.

DNA Sequence Analysis of Candidate SNPs.

Genomic DNA samples that were determined by DMA to contain a SNP were amplified using PCR and the products purified as described above to eliminate excess primer and genomic DNA. The sequencing reaction was performed in a 10 µl reaction containing 10 nM of one primer (forward or reverse), 4 µl of BigDye™ Terminator Cycle Sequencing reaction mixture (Perkin Elmer), and 3 µl of the purified PCR product. The temperature cycle for the sequencing reaction consisted of 25 cycles of 10 sec at 96° C., five sec at 56° C., and four min at 60° C. Purification of this reaction was performed using a gel filtration block (AGTC). The purified reaction products were vacuum dried and resuspended in formamide and sequencing dye mix. Products were resolved on an ABI 377 automated sequencer. The determined sequence was aligned and analyzed using the ABI AutoAssembler software.

Results

To determine the effect of SYBR dye concentration, DNA concentration, and fragment length on duplex DNA melting, a polymorphism located in the first exon of the 5-HT2a receptor (HTR2A) nucleic acid (102T>C, Genbank accession X57830) was analyzed. The melting profiles of DNA homoduplexes were compared to mixtures of homoduplexes and heteroduplexes that naturally result from the amplification or synthesis of heterozygous dsDNA and its denaturation and slow re-annealing.

Figure 2:
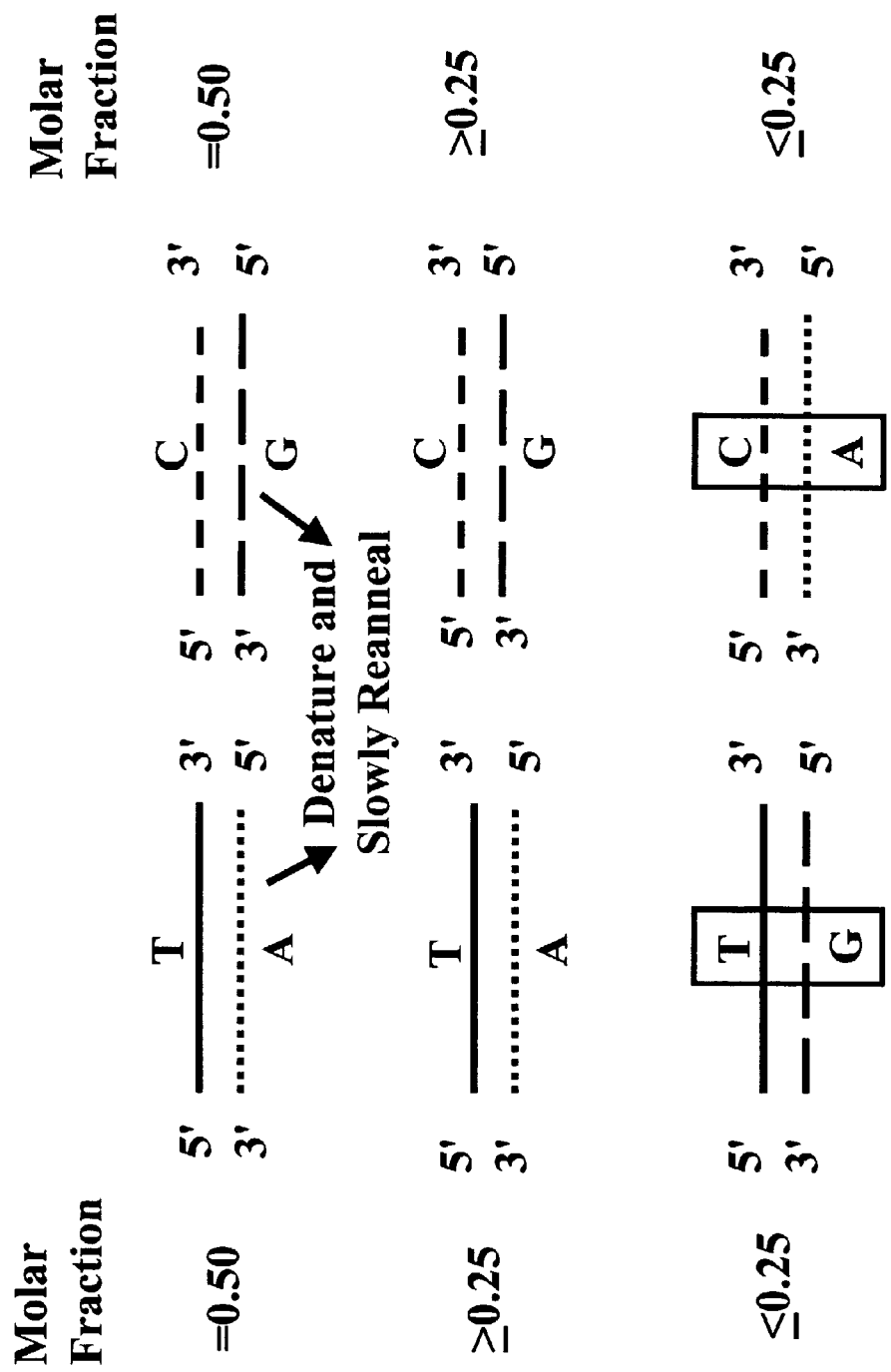
FIG. 2 is a schematic illustration of DNA melting analysis (DMA). Denaturation and reannealing of heterozygous DNA (top row) leads to a mixture of four duplex DNAs. The dsDNA is composed of two different homoduplexes (middle row) and two different heteroduplexes (bottom row). Because of the thermodynamics of reannealing, the homoduplex DNA represents at least 50% of the total amount, whereas the heteroduplex DNA is at most 50% of the total duplexes. Mismatches in the heteroduplex DNA are represented by open boxes.

As shown in FIG. 2, amplification, denaturation and re-annealing of heterozygous DNA will yield four dsDNA duplexes. The two homoduplexes constitute at least 50% of the re-annealed dsDNA, and the two heteroduplex DNAs constitute at most 50% of the re-annealed dsDNA.

Each of the four dsDNA species formed during re-annealing has different thermodynamic characteristics. For small DNA duplexes, G-T mismatches are less thermodynamically destabilizing than A-C mismatches. See, e.g., Allawi, H. T., and SantaLucia J., Biochemistry 36:10581-94 (1997). However, the magnitude of the difference in melting thermodynamics of the two heteroduplex DNA species makes them readily distinguishable from either of the homoduplex dsDNAs.

Concentration of DNA and SYBR.

Increasing DNA concentration increases the $T_m$ of duplex DNA in solution, thus implicating the ability to detect sequence variation by DMA. Therefore, since double-strand DNA concentrations can vary as a result of different efficiencies in PCR amplification or other amplification of DNA, some embodiments employ solutions having substantially similar concentrations for comparing melting profiles.

Figure 3A:
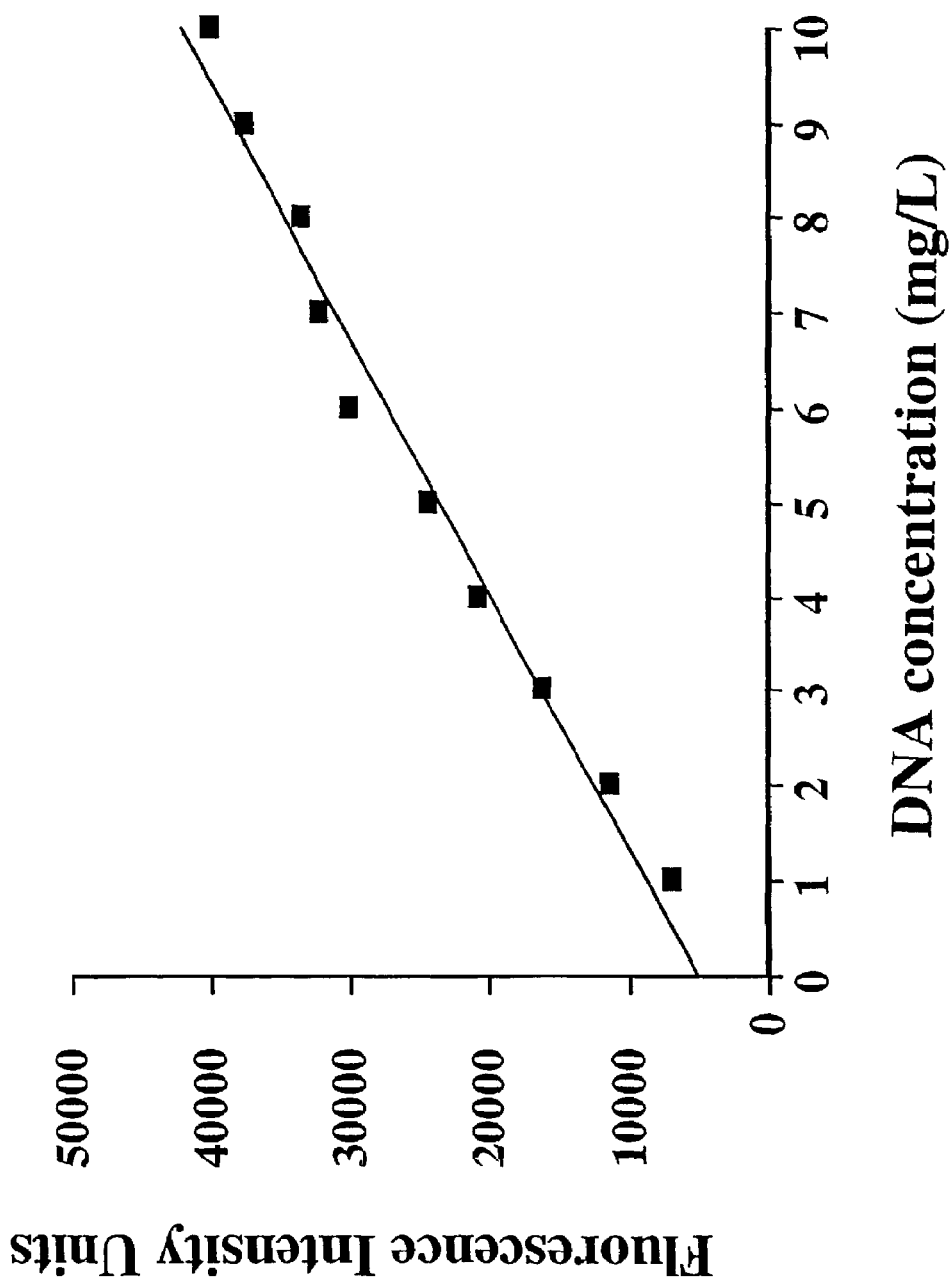
FIGS. 3A-C are graphs illustrating the measurement of dsDNA concentration with SYBR dye, a dsDNA specific fluorescent dye. dsDNA was taken from a 100-bp amplicon of the human HTR2A nucleic acid.
Figure 3B:
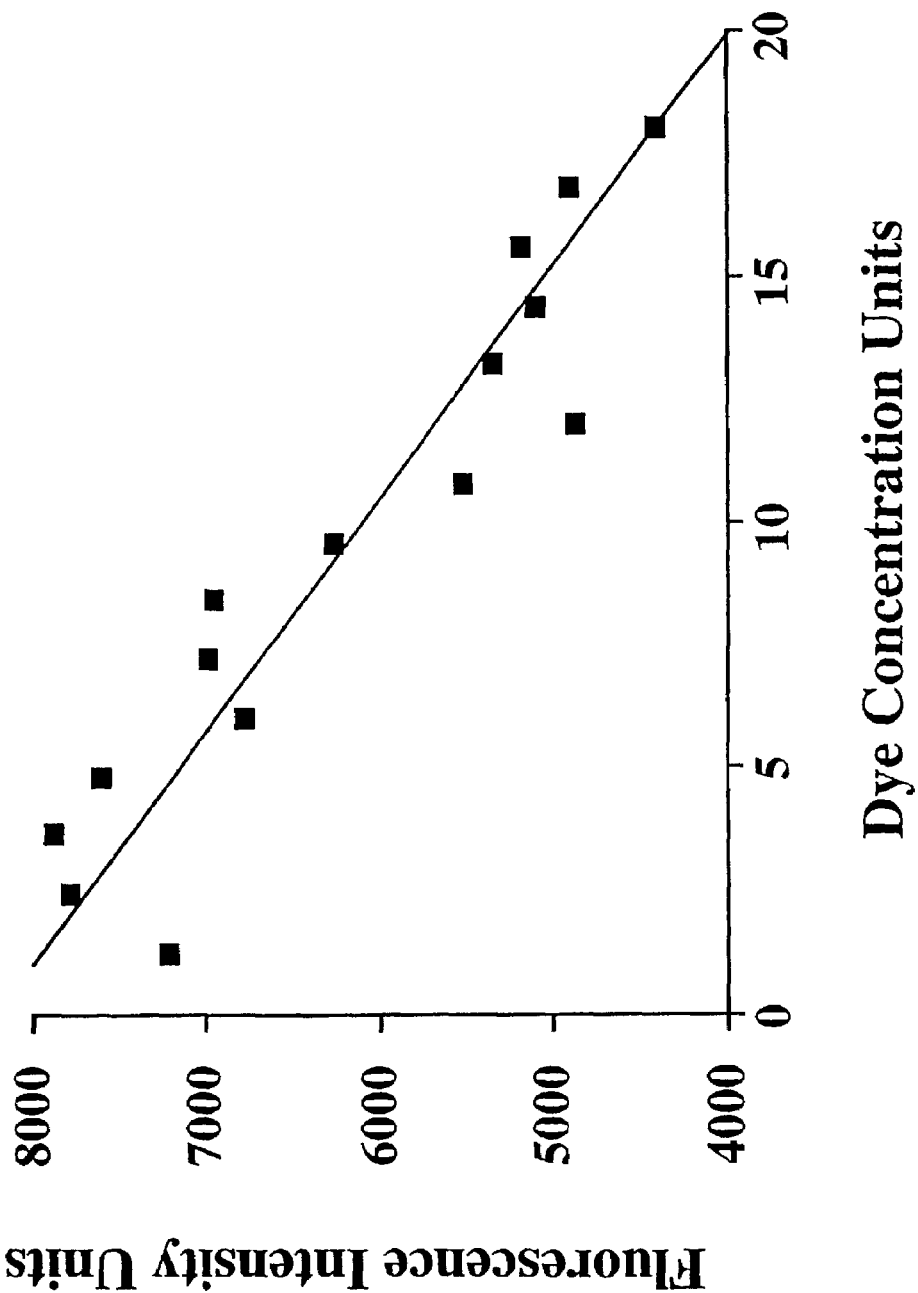
Figure 3C:
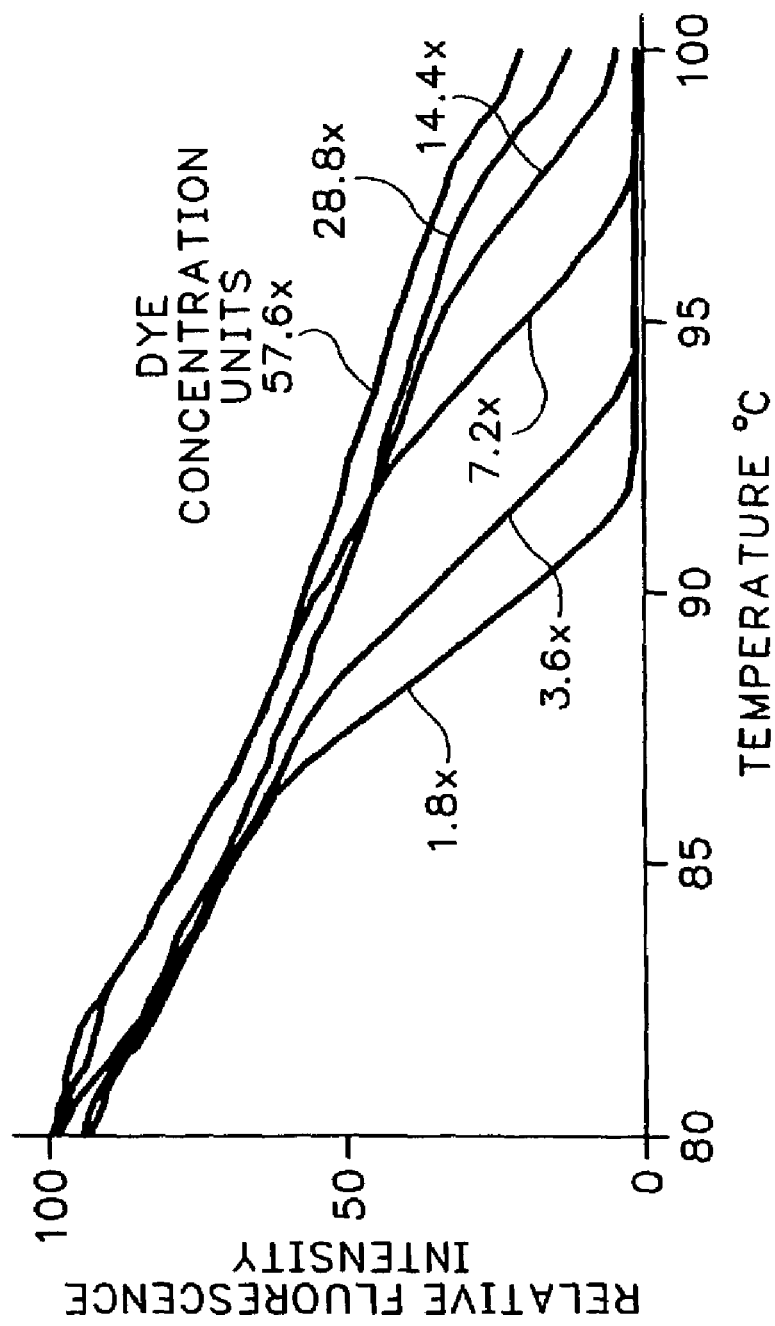

To approach this issue, the extent of variation in initial dsDNA concentrations prior to melting was monitored using the HTR2A 100 bp amplicon. As shown in FIG. 3A, DNA concentration could be measured on the ABI 7700 by monitoring SYBR fluorescence intensity, because this intensity is linearly proportional to dsDNA concentration. Additionally, higher concentrations of SYBR dye quenched the fluorescence signal (FIG. 3B).

Double-strand DNA quantitation revealed that the concentration of a particular DNA amplicon was highly reproducible as determined by the SYBR fluorescence signal. The coefficient of variation for different DNA concentrations of the HTR2A 100 bp amplicon was 2.6%. Thus, amplicon concentrations were highly reproducible. Similar results also were obtained for different amplicons using different primer combinations. Therefore, DNA concentrations could be reliably monitored in all of the samples prior to melting analysis using the same device in which melting analysis was conducted, such as the ABI 7700.

Increasing the dsDNA concentration increased the $T_m$ of the 100 bp HTR2A amplicon. In the presence of SYBR dye, as DNA concentration was increased from 0.5 ng/µl to 10 ng/µl, the melting curves were shifted to the right, as expected.

The effect of different concentrations of SYBR dye on the temperature of dsDNA denaturation was evaluated (FIG. 3C) using the HTR2A 100 bp amplicon at a concentration of 2 ng/µl in a 15 µl final assay volume. This was a convenient DNA concentration given that the typical yield of a PCR reaction was about 10 ng/µl in a volume of 30 µl.

SYBR dye, supplied as a 10,000× stock, was suggested by the manufacturer to be used after diluting ¹⁄₁₀,₀₀₀. We determined that a suitable dye concentration for a wide range of DNA concentrations was 3.6×. Some lower SYBR concentrations led to low emission signals, but some higher dye concentrations resulted in signal quenching. In addition, increasing the concentration of SYBR dye from 1.8× to 57.6× shifted the DNA melting curve to the right, indicating that by binding the dsDNA, the dye stabilizes the DNA duplex, thereby increasing the temperature at which it is denatured. In fact, at particularly high SYBR dye concentrations relative to a constant DNA concentration, the dsDNA did not completely denature, as evidenced by the melting curves obtained using 28.8× and 57.6× SYBR dye (FIG. 3C), which are shifted far to the right.

Ability to Detect Single Base Mismatches in DNA Fragments of Different Length.

Figure 5A:
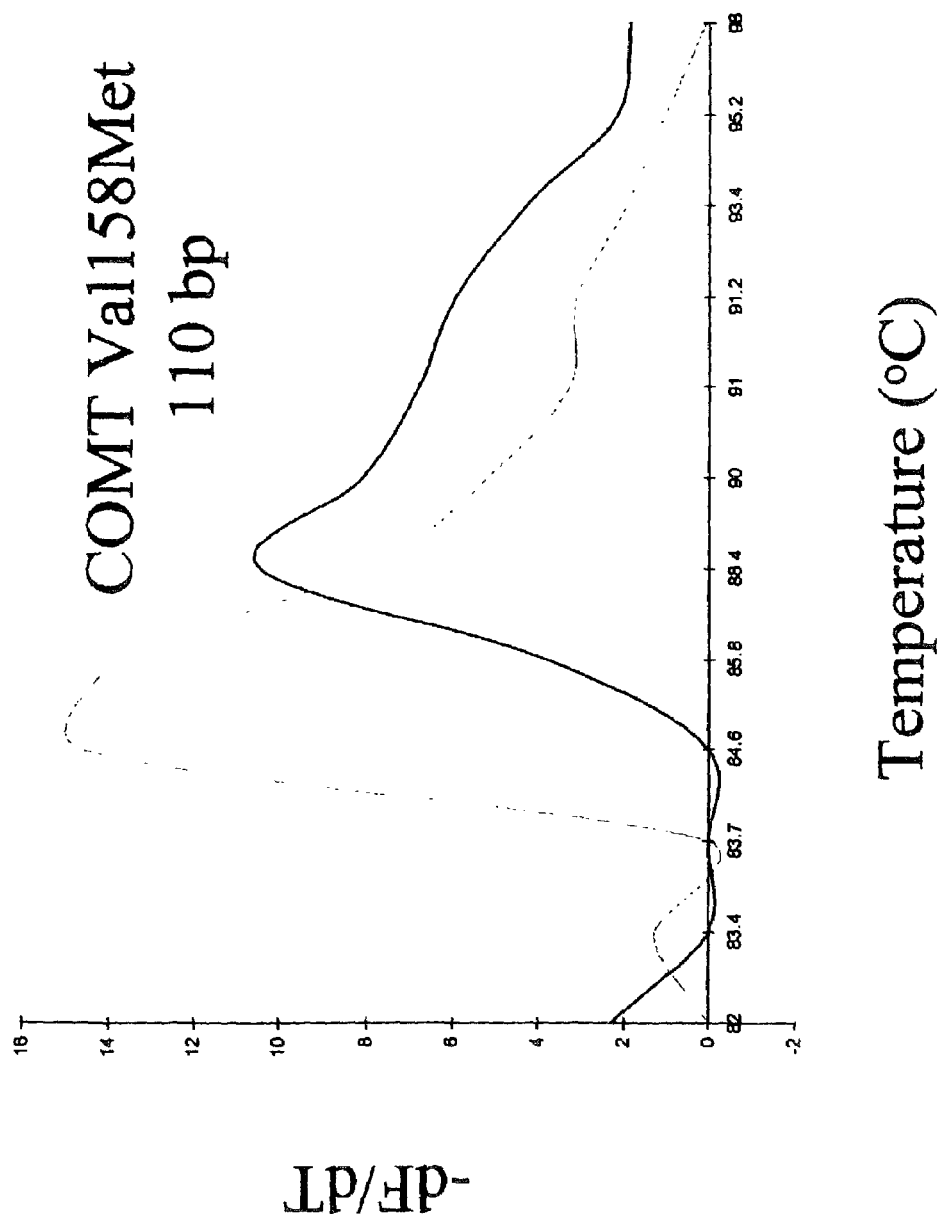
FIGS. 5A-C are graphs illustrating the detection of two SNPs and a single nucleotide deletion using DMA.
Figure 5B:
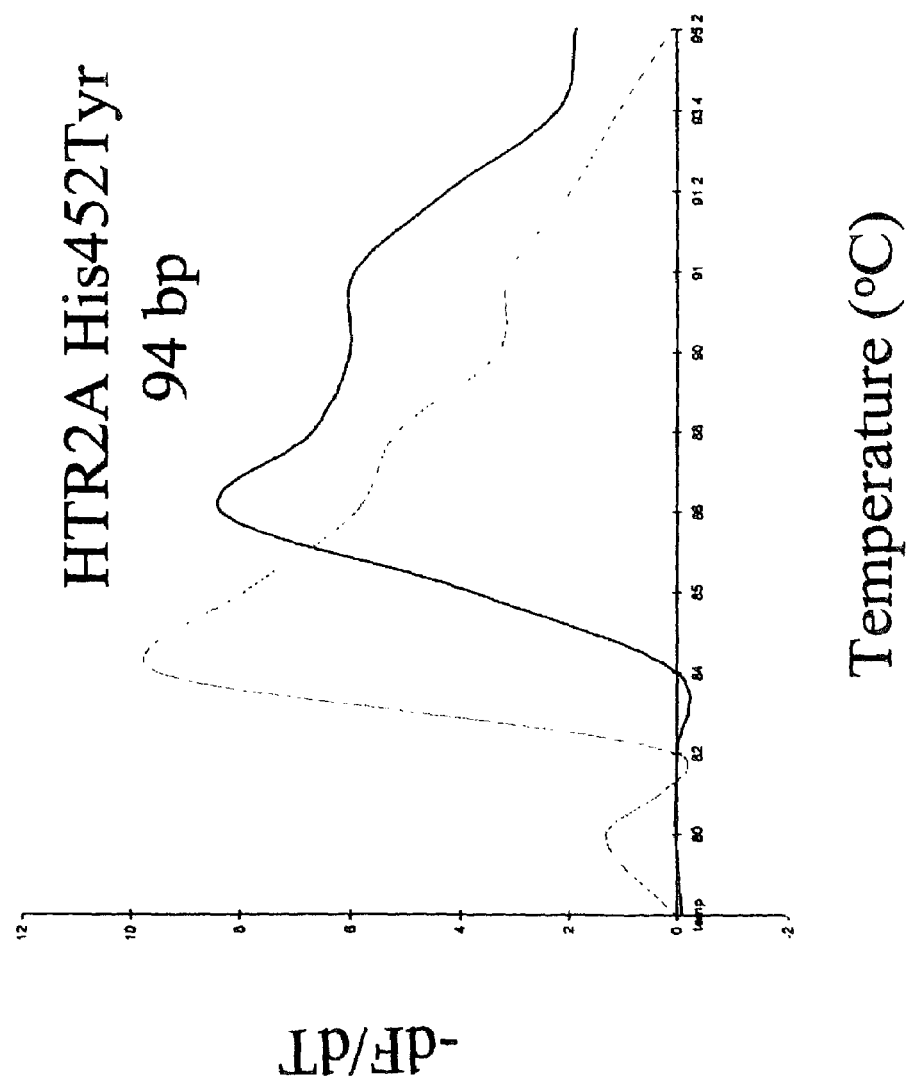
Figure 5C:
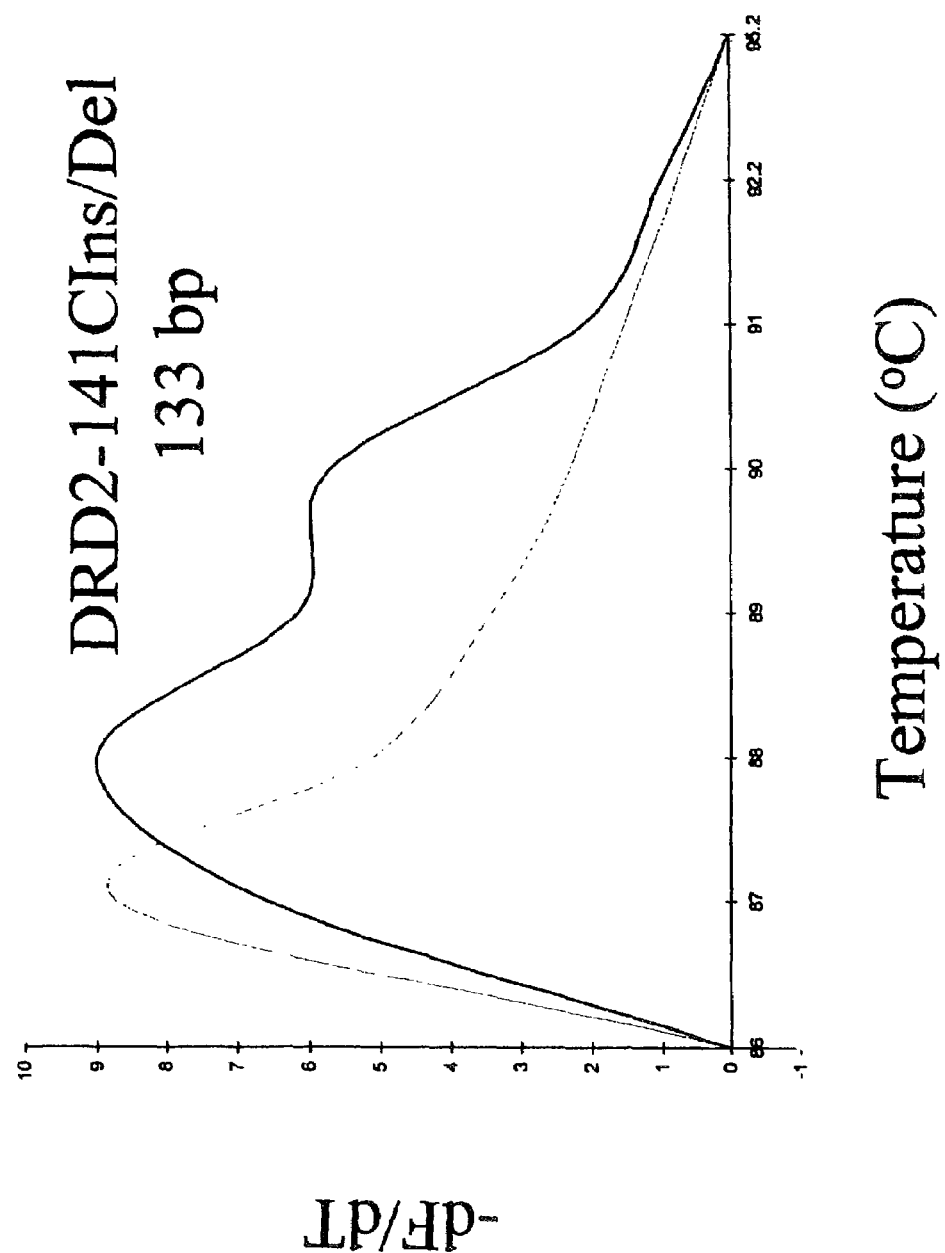

Six dsDNA HTR28 fragments of different lengths were either synthesized (15 bp; SEQ ID NOS: 1-4 and 25 bp) or PCR amplified (60 bp, 80 bp, 100 bp, and 152 bp) by primers provided in SEQ ID NOS: 5-14. All fragments had the same T>C polymorphism located in the middle of the same target HTR2A nucleic acid sequence. The effect of the single base pair mismatches (G•T and A•C) was assessed by comparing the thermodynamic stability of the DNA heteroduplexes to homoduplex DNA (A•T). A 97 bp fragment also was amplified in which the mismatch was located 30 bp from the 5' end (see Table 1).

insertion/deletion used was DRD2-141C Ins/Del (Genbank accession X53502) in a 133 bp fragment (FIG. 5C).

In each of these instances, the homoduplex/heteroduplex mixture produced derivative melting profiles that were distinguishable from the melting profiles for the homoduplex (FIGS. 5A-C). The homoduplex/heteroduplex mixtures

TABLE 1

Physical characteristics of DNAs analyzed by DMA

| Gene | SNP | Amino acid substitution | Fragment size,[a] bp (% GC) | NSP nt[b] position witin fragment | Predicted $\Delta T_m$[c] ° C. (homoduplex-heteroduplex) | Observed $\Delta T_m$[c] ° C. (homoduplex-heteroduplex) |
|---|---|---|---|---|---|---|
| HTR2A | 102T→C[d] | | 15(40) | 8 | 2.9; 5.4 | 4.9 |
| | 102T→C[d] | | 25(40) | 13 | 2.4; 5.8 | 3.5 |
| | 102T→C | | 60(40) | 30 | 0.7; 1.8 | 5.5 |
| | 102T→C | | 78(40) | 41 | 0.5; 1.3 | 5.0 |
| | 102T→C | | 97(43) | 31 | 0.4, 1.0 | 2.8 |
| | 102T→C | | 100(41) | 42 | 0.9; 1.5 | 1.4 |
| | 102T→C | | 152(43) | 68 | 0.2; 0.6 | 0.9 |
| | 1499C→T | His452Tyr | 94(44) | 51 | 0.9; 1 3 | 2.6 |
| COMT | 1947G→A | Val158Met | 110(59) | 66 | 0.6; 0.6 | 3.8 |
| DRD2-141C | Ins/del | | 133(67) | 43 | NP | 1.2 |
| NR1[e] | 3680C→T | Ala310Val | 163(60) | 86 | 0.5; 0.7 | 2.2 |
| AChR[e] | 147G→T | | 167(58) | 131 | 0.2; 0.6 | 0.6 |

[a]Nonvariant fragment.
[b]nt nucleotide; NP, no prediction from MeltCalc.
[c]Based on Tm predictions for each of two heterduplexes using MeltCalc software of Shütz and von ahsen (17).
[d]15- and 25-bp fragments were chemically synthesized, and the remainder were PC amplicons.
[e]SNPs discovered during this study.

When the 15 bp or the 25 bp dsDNA fragments were subjected to a temperature increase of 2° C./minute, a readily observable difference in the rate of decrease in SYBR fluorescence was observed between homoduplex dsDNA compared to the heteroduplex/homoduplex DNA mixture. The fluorescence data from each melting curve was converted into melting peaks ($T_m$) by plotting the negative derivative of fluorescence versus temperature (–dF/dT vs T). Thus, a rate of decrease in SYBR florescence corresponds to an increase in the proportion of ssDNA within a sample.

Figure 4A:
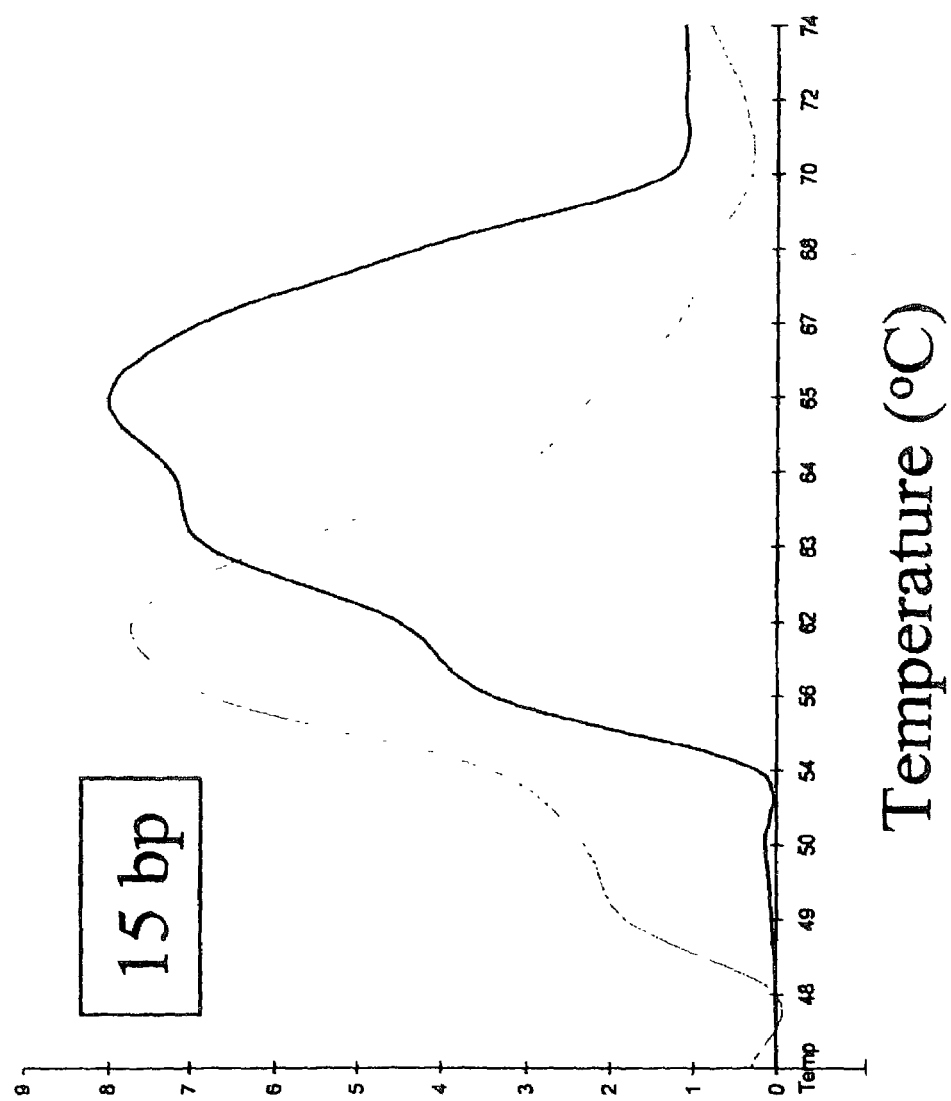
FIGS. 4A-D are graphs illustrating the detection of single nucleotide mismatches in dsDNA fragments of different sizes. The melting profiles of dsDNAs of increasing size containing the HTR2A 102T C SNP are shown, and in each graph, the temperature increases from left to right.

A representative derivative plot for the 15 bp fragment is shown in FIG. 4A. The difference in $T_m$ ($\Delta T_m$) between homoduplex DNA and heteroduplex/homoduplex mixture was approximately 5° C. for the 15 bp fragment and 3.5° C. for the 25 bp fragment (FIG. 4A, Table 1). Each observed value was within the range of values of A $T_m$ predicted for that fragment (Table 1).

Figure 4B:
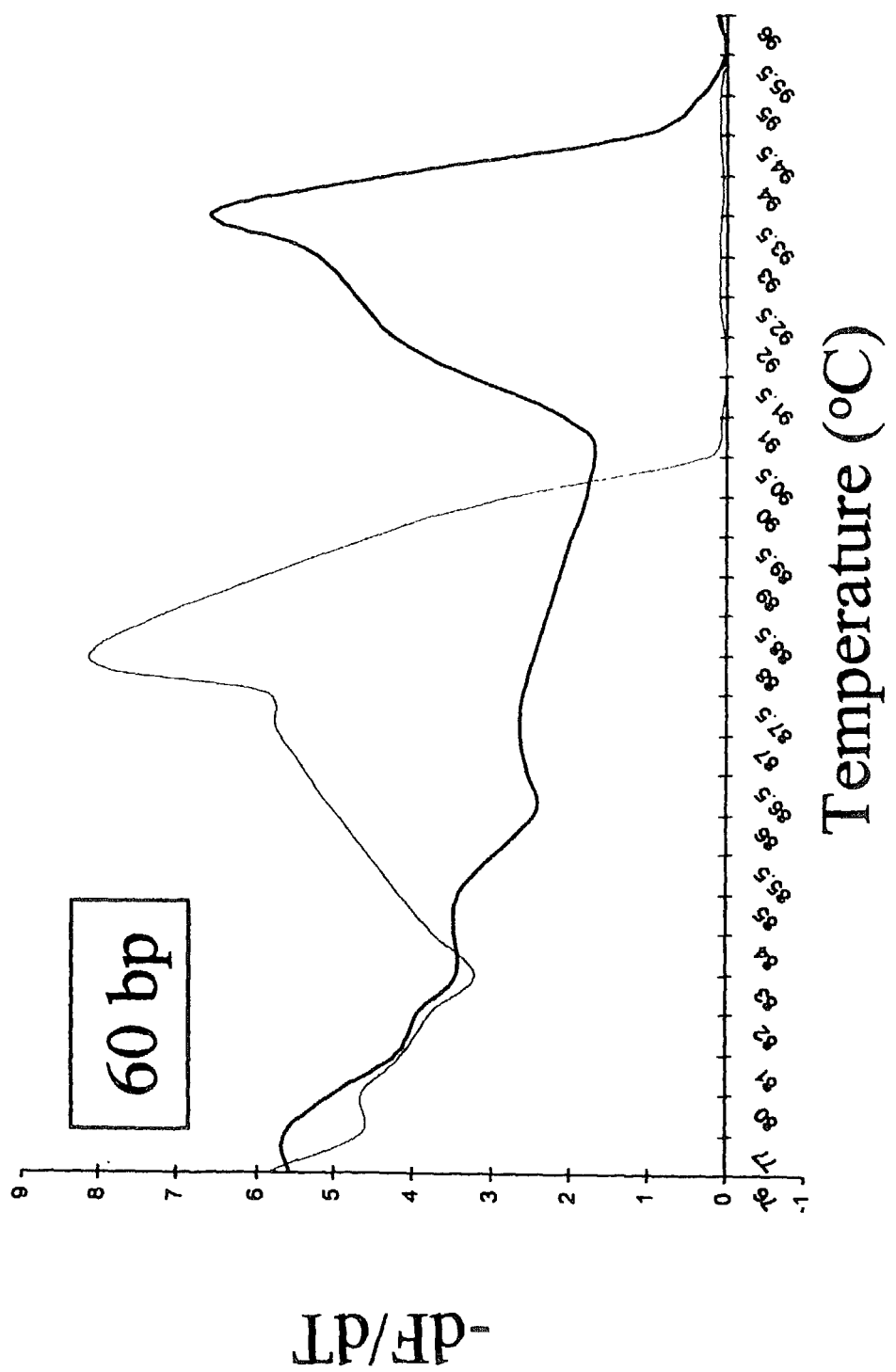
Figure 4C:
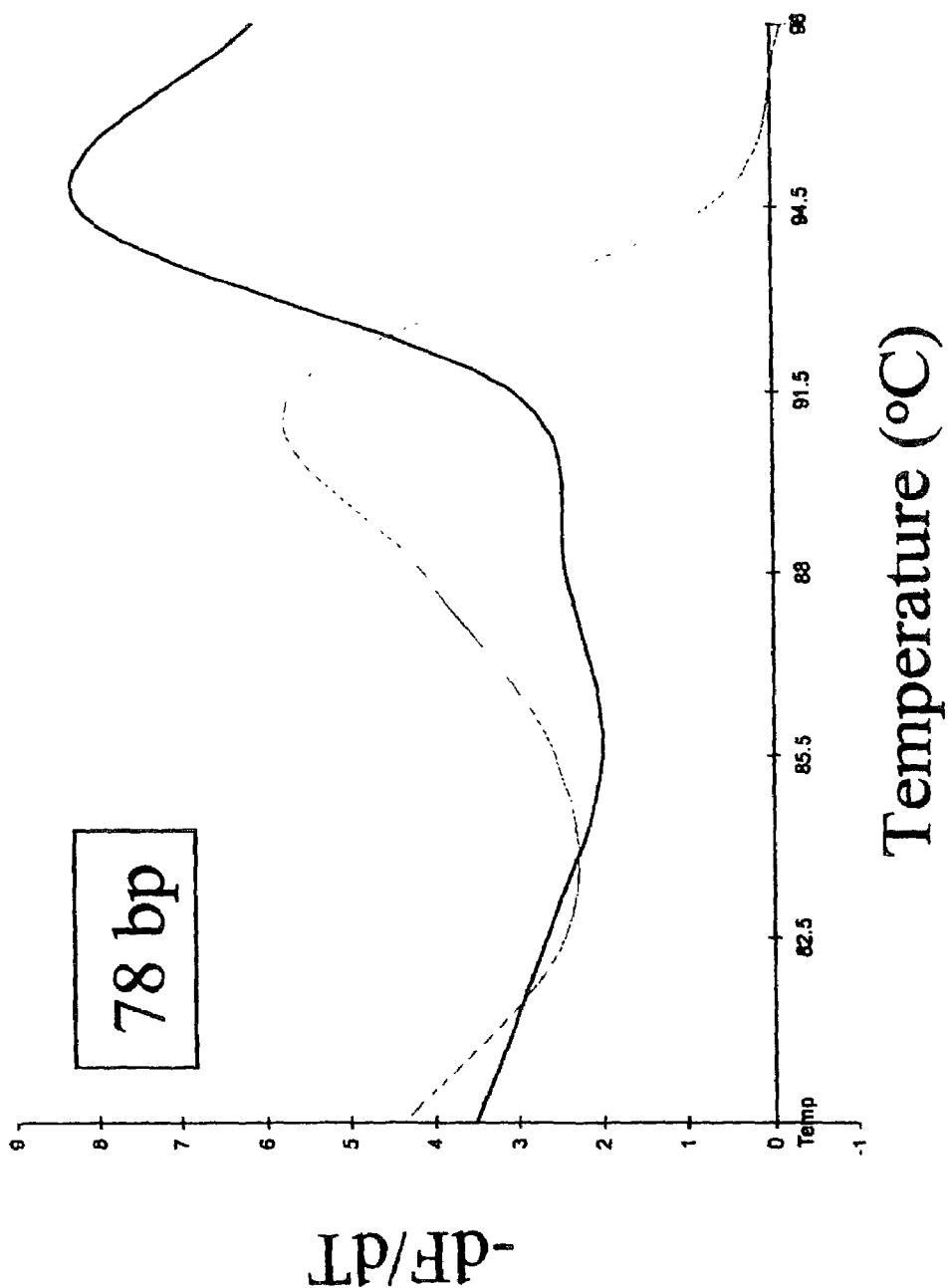
Figure 4D:
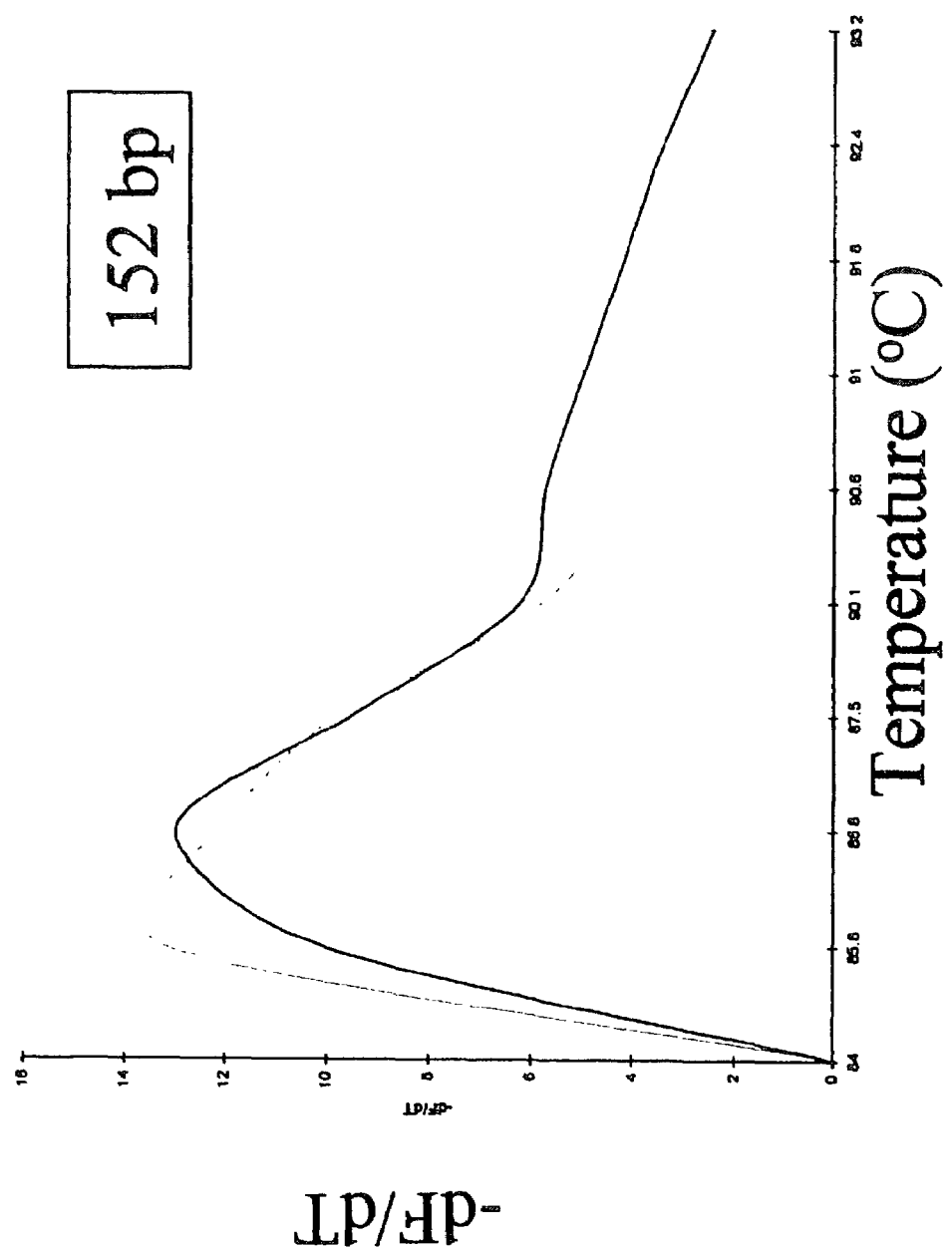

For longer dsDNAs, the rate of DNA melting was decreased to 0.5° C./minute for 60 bp and 80 bp fragments, and to 0.067° C./minute for fragments 97-152 bp in size. The differences in the melting rates among homoduplex dsDNA and the heteroduplex/homoduplex mixture were again readily distinguishable. The observed $\Delta T_m$ for these fragments varied between 0.9° C. (152 bp) and 5.5° C. (60 bp) (FIGS. 4B-4D, Table 1).

Detection of Additional Sequence Variants Using DNA Melting Analysis (DMA).

Two additional SNP variants and a single nucleotide insertion/deletion were also examined by DMA using amplicons of 94 bp, 110 bp, and 133 bp in size. The SNPs, both of which result in amino acid substitutions, were HTR2A 1499C→THis452Tyr (Genbank accession X57830) and COMT 1947G→AVal158Met (Genbank accession Z26491) in fragment sizes of 94 bp and 110 bp, respectively. The exhibited lower melting temperatures ($T_m$, at the peak of the curve) compared to the $T_m$ of the homoduplex (FIGS. 5A-C). The observed $\Delta T_m$ for each amplicon heteroduplex ranged from 1.2° C. to 3.8° C. (Table 1).

Example 2

SNP Detection

Using the protocols described in Example 1, the existences of SNPs were analyzed and investigated by comparison to dHPLC.

Amplicon sizes were selected that could be easily screened by dHPLC and derived from portions of two different nucleic acids: (1) exon sequences of NR1; and (2) exon and intron sequences from AChR. The two PCR amplicons were 163 bp (NR1) and 167 bp (AChR) in size and were amplified from genomic DNA prepared from six unrelated subjects.

The PCR products were thermally denatured and allowed to re-anneal, then assessed by DMA. The melting profile of each sample was determined and the fluorescence data from melting curves were then plotted on a graph by conversion to melting peaks ($T_m$) using the derivative melting profile (–dF/dT vs T). See FIGS. 6A and 7A.

One sample from the NR1 nucleic acid amplification and one sample from the AChR nucleic acid amplification, each originating from a different subject, showed a significant $T_m$ shift when compared with the melting peaks obtained for the other NR1 nucleic acid or AChR nucleic acid-derived samples. These results suggested the presence of heteroduplex/homoduplex DNAs. These melting profiles were repeated with similar results. The observed $\Delta T_m$ for these fragments were 2.2° C. (163 bp NR1) and 0.6° C. (167 bp AChR). See Table 1.

Figure 8A:
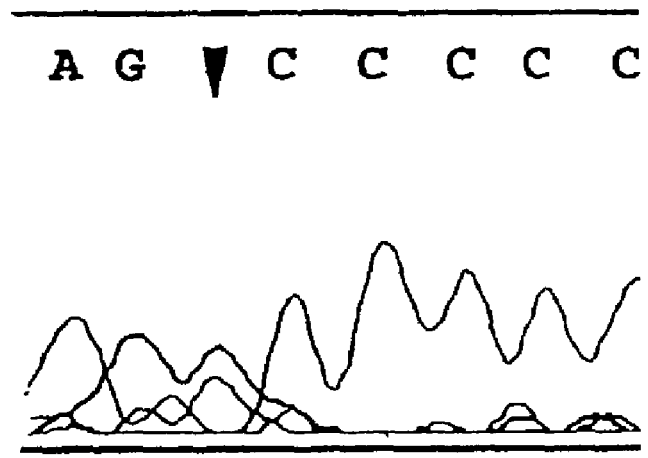
FIGS. 8A-B are electrophoretograms illustrating the primary nucleotide sequence determined from a PCR product obtained from a subject heterozygous for an SNP in the AChR nucleic acid sequence (FIG. 8A) and a subject heterozygous for an SNP located at position 3680 of the NR1 nucleic acid sequence (FIG. 8B).
Figure 8B:
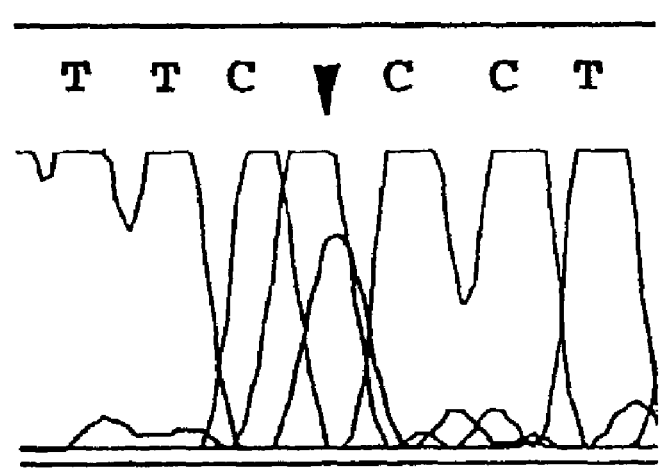

The two genomic DNA samples that produced the $T_m$ shifts were then independently amplified for DNA sequence analysis. Direct DNA sequence analysis of these PCR products showed the presence of an SNP within the amplicon (FIG. 8). No other variants were detected in either of these PCR products.

Figure 6A:
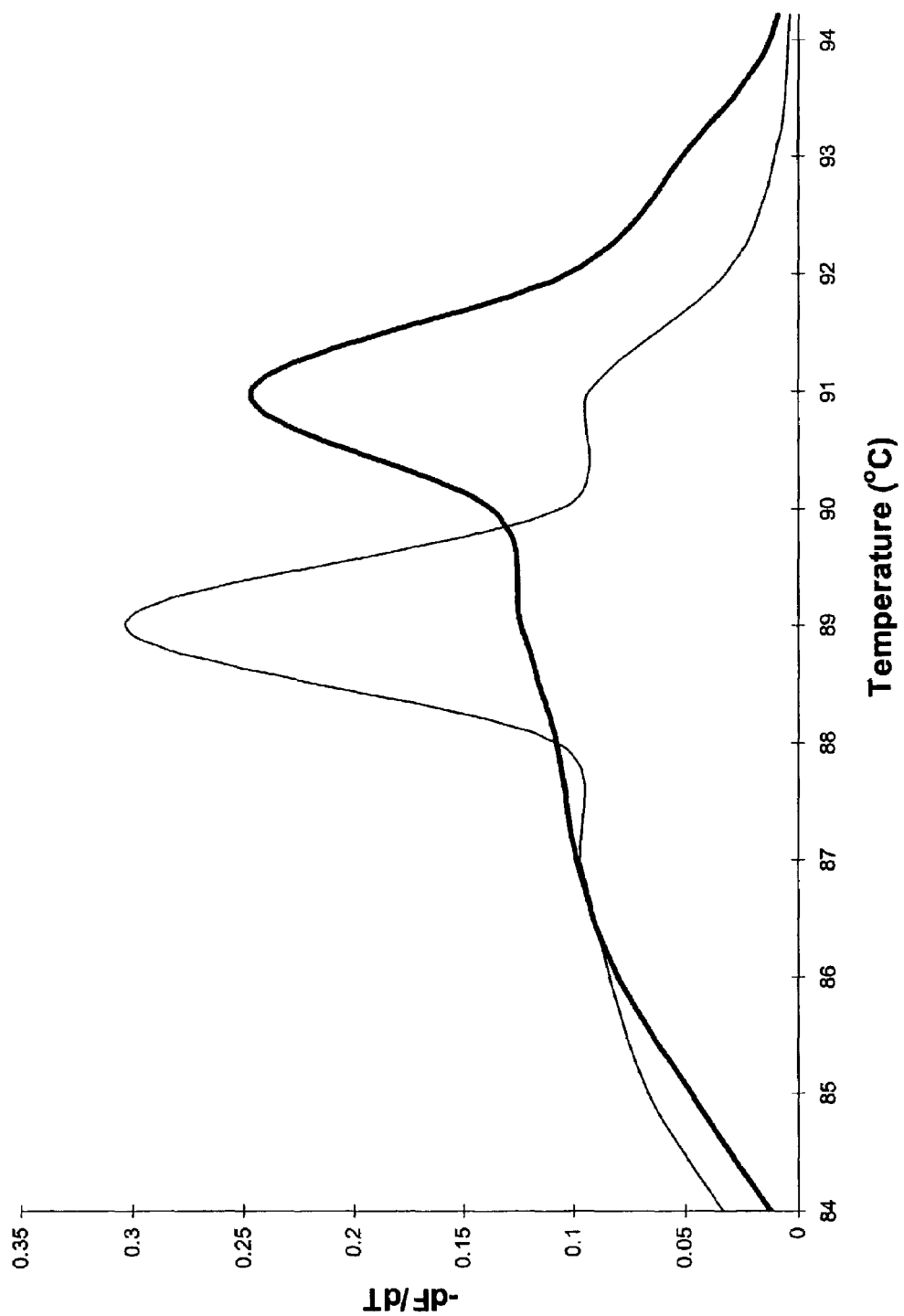
FIGS. 6A-B are graphs illustrating a melting profile of a PCR amplicon amplified from the human NR1 nucleic acid sequence. The conditions used for the DMA of FIG. 6A were: dsDNA concentration of 2 mg/L; SYBR dye concentration of 3.6x; and a melting rate of 0.067° C./minute. Fluorescence data were converted into $T_m$ by plotting the negative derivative of fluorescence versus temperature (−dF/dT vs T). The homoduplex melting curve is depicted by a thick line, while the melting curve for the heteroduplex/homoduplex mixture is shown as a thin line.
Figure 6B:
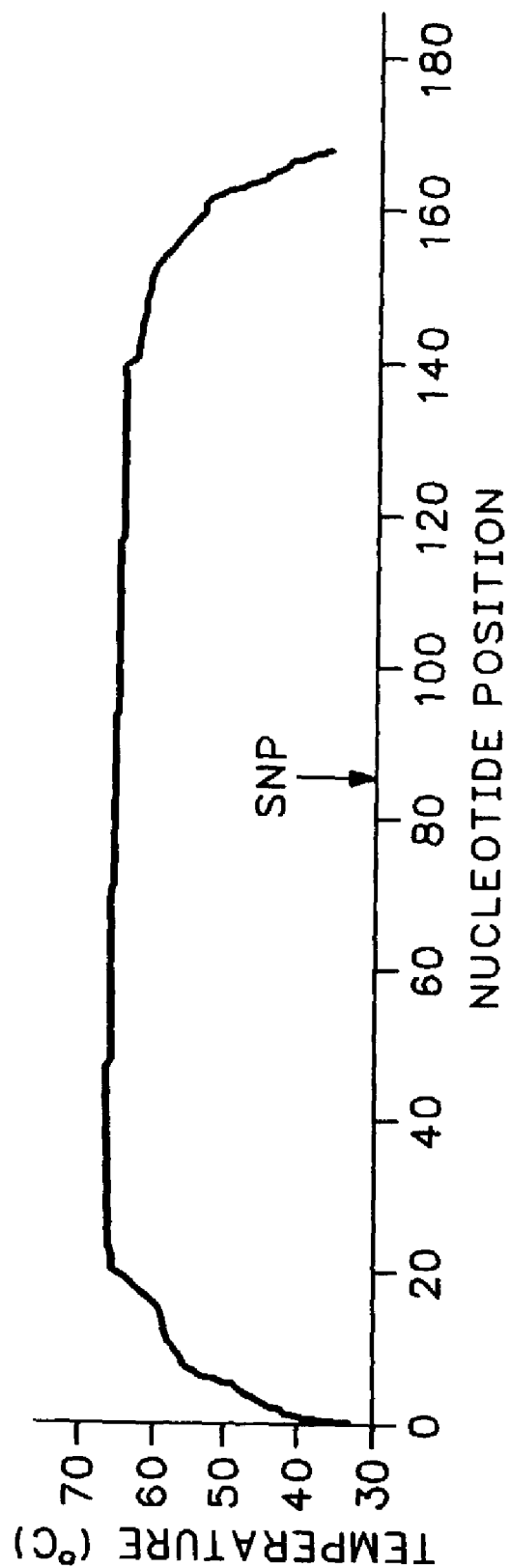
Figure 7A:
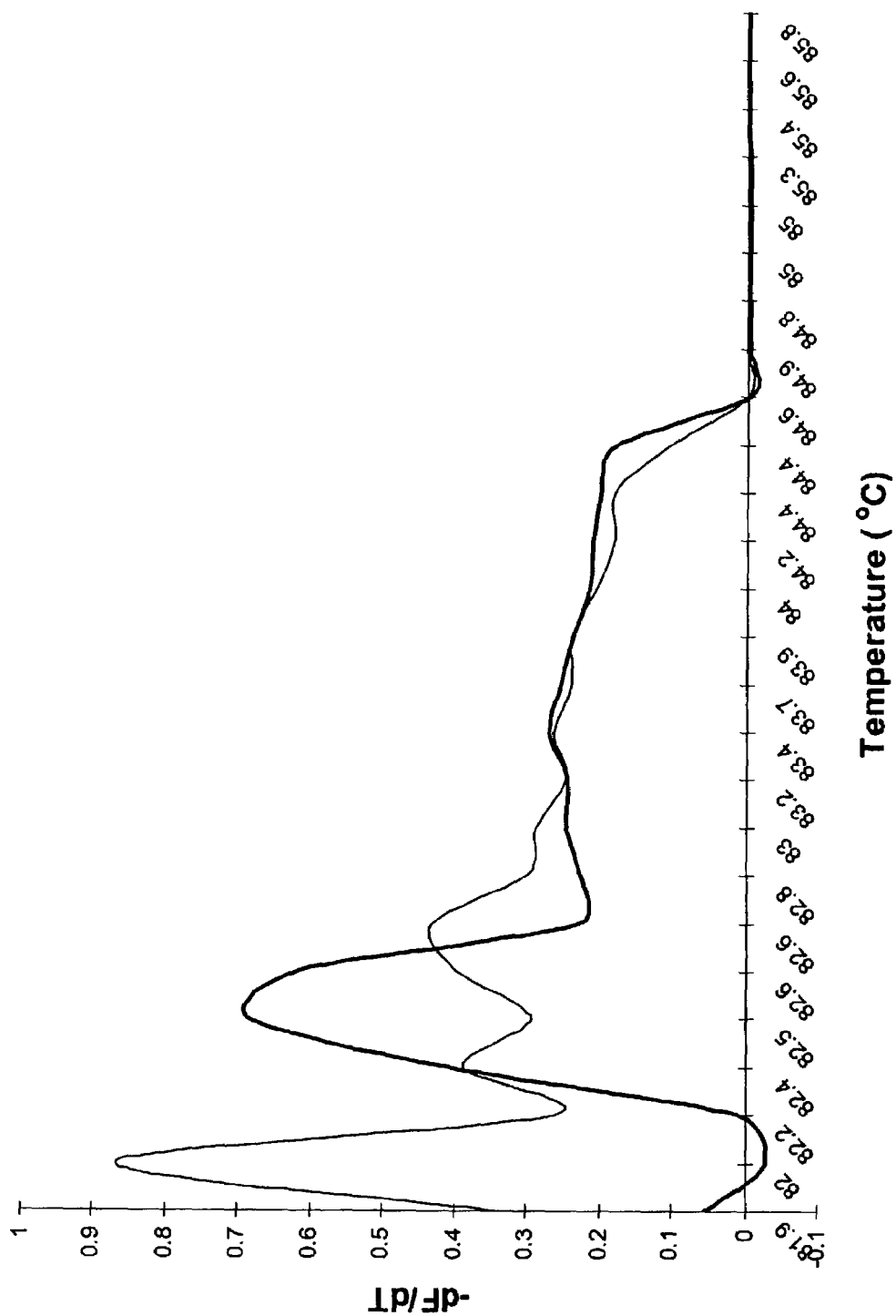
FIGS. 7A-B are graphs illustrating a melting profile of a PCR amplicon from the human AChR nucleic acid sequence used for detecting of an unknown SNP. The conditions used for the DMA of FIG. 7A were: dsDNA concentration of 2 mg/L; SYBR dye concentration of 3.6x; and a melting rate of 0.067° C./minute. Similar to FIGS. 6A-B, fluorescence data are presented as the negative derivative of fluorescence versus temperature (−dF/dT vs T). Peaks in each curve represent the melting temperature ($T_m$). The homoduplex melting profile is depicted with a thick line, while the heteroduplex/homoduplex mixture melting profile is shown by a thin line.
Figure 7B:
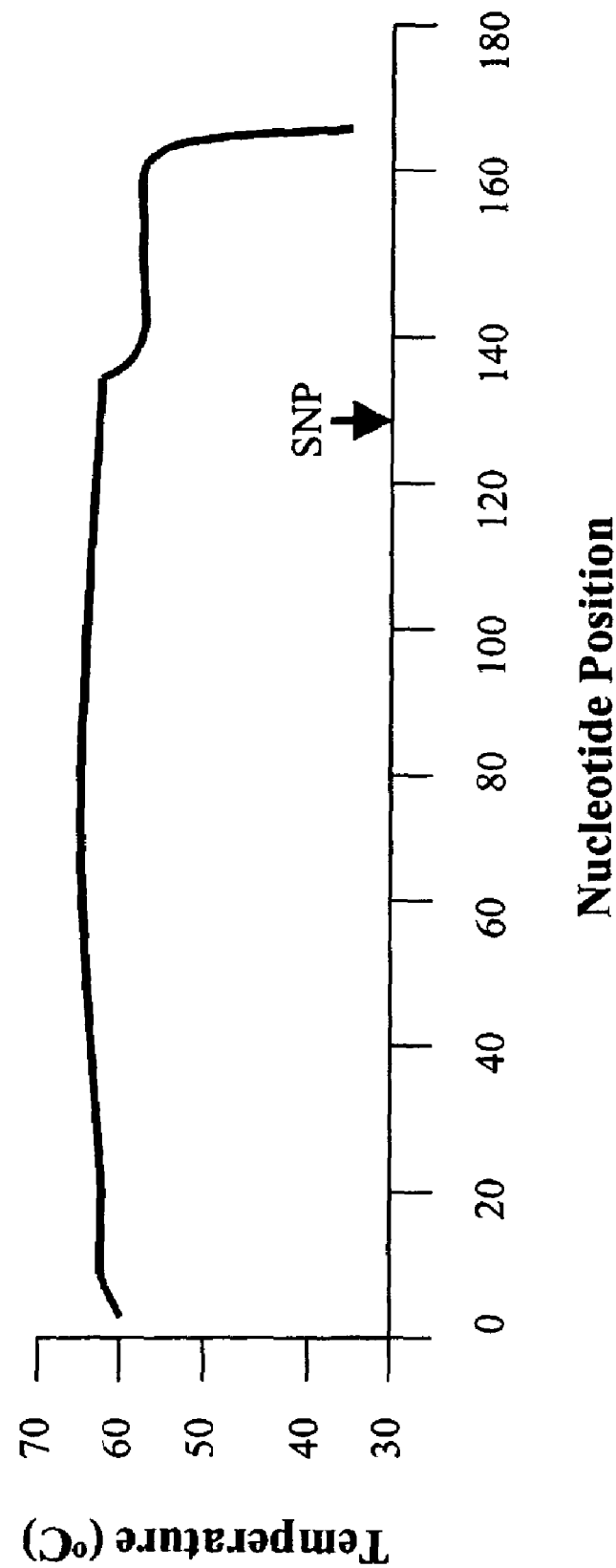

Direct sequencing of the NR1 or AChR PCR products not showing a $T_m$ shift that showed no existence of an SNP within the amplicon. Additionally, the new SNPs discovered in the NR1 and AChR nucleic acids by DMA were replicated using dHPLC, and each SNP was located in a region of the PCR amplicon that was predicted to behave as a single melting domain (FIGS. 6B and 7B).

Having illustrated and described the principles of the invention by several embodiments, it should be apparent that those embodiments can be modified in arrangement and detail without departing from the principles of the invention. Thus, the invention includes all such embodiments and variations thereof, and their equivalents.

We claim:

1. A method of detecting a nucleic acid sequence variation, wherein the sequence variation is a single-nucleotide polymorphism or a 1 nucleotide deletion, insertion or inversion, comprising:

denaturing a first double-stranded nucleic acid and a second double-stranded nucleic acid, wherein the first double-stranded nucleic acid and the second double-stranded nucleic acid are each at least about 152 bp, and wherein the first double-stranded nucleic acid and the second double-stranded nucleic acid do not include a GC-clamp, thereby generating denatured nucleic acids in solution;

allowing the denatured nucleic acids to reanneal, thereby generating reannealed nucleic acids in solution;

increasing the temperature of the reannealed nucleic acids at a rate of about 0.067° C./minute or less;

detecting a transition of the reannealed nucleic acids between a double-stranded state and a single-stranded state, thereby generating a melting profile for the reannealed nucleic acids; and comparing the melting profiles of the reannealed nucleic acids wherein a difference between the melting profiles of the reannealed nucleic acids indicates a sequence variation between the first double-stranded and second double-stranded nucleic acids.

2. The method according to claim 1 wherein the first double-stranded nucleic acid comprises a homoduplex nucleic acid and the second double-stranded nucleic acid comprises a heteroduplex nucleic acid.

3. The method according to claim 2 wherein the solution comprising the denatured nucleic acids further comprises another homoduplex double-stranded nucleic acid.

4. The method according to claim 1, further comprising amplifying the first or second double-stranded nucleic acid.

5. The method according to claim 1 wherein the nucleic acid concentration of the solution comprising the denatured nucleic acids is from about 0.8 mg/L to about 4.0 mg/L.

6. The method according to claim 1 wherein the GC content of the first double-stranded nucleic acid is less than about 70%.

7. The method according to claim 6 wherein the GC content of the first double-stranded nucleic acid is less than about 50%.

8. The method according to claim 1 wherein detecting the transition comprises fluorescence detection by:

adding a fluorescent dye to the solution comprising the reannealed nucleic acids; and detecting a fluorescent signal emitted from the solution comprising the reannealed nucleic acids, wherein a difference between or among the fluorescent signals emitted from the solution comprising the reannealed nucleic acids at the same temperature indicates a difference between or among the melting profiles of the-reannealed nucleic acids.

9. The method according to claim 8 wherein the fluorescent dye is SYBR Green dye at a concentration of about 1.0× to about 5.0× relative to a 10,000× dye concentrate.

10. The method according to claim 9 wherein the dye concentration is about 1.8× to about 3.6× relative to a 10,000× dye concentrate.

11. The method according to claim 10 wherein the dye concentration is about 3.6× relative to a 10,000× dye concentrate.

12. The method according to claim 1 wherein the first or second double-stranded nucleic acid is DNA.

13. The method according to claim 1 wherein the first double-stranded nucleic acid is at a concentration from about 0.5 mg/L to about 10.0 mg/L in the solution comprising the denatured nucleic acids.

14. The method according to claim 13 wherein the first double-stranded nucleic acid is at a concentration of about 2 mg/L in the solution comprising the denatured nucleic acids.

15. The method according to claim 1 wherein at least one of the first or second double-stranded nucleic acids has been obtained from a mammal.

16. The method according to claim 15 wherein the mammal is a human.

17. A method of detecting a nucleic acid sequence variation, wherein the sequence variation is a single-nucleotide polymorphism or a 1 nucleotide deletion, insertion or inversion, comprising:

amplifying a first nucleic acid to produce a first amplicon having a length of about 152 bp or greater and amplifying a second nucleic acid to produce a second amplicon having a length of about 152 bp or greater, wherein the first and second amplicons do not include a GC-clamp;

diluting the first amplicon in a first solution and diluting the second amplicon in a second solution, wherein the nucleic acid concentrations of the first and second solutions are substantially the same;

determining melting profiles for the first and second amplicons using a temperature transition rate of about 0.067° C./minute or less for denaturation, wherein a difference between the melting profiles indicates a nucleic acid sequence variation between the first and second amplicon nucleic acid sequences.

18. The method according to claim 17 wherein the nucleic acid concentration of the first solution is from about 0.5 mg/L to about 10 mg/L.

19. The method according to claim 18 wherein the nucleic acid concentration of the first solution is about 2.0 mg/L.

20. The method according to claim 17 wherein the GC content of the first amplicon is less than about 70%.

21. The method according to claim 20 wherein the GC content of the first amplicon is less than about 50%.

22. A method of detecting a nucleic acid sequence variation within an away of nucleic acids, wherein the sequence variation is a single-nucleotide polymorphism or a 1 nucleotide deletion, insertion or inversion, comprising:
  denaturing plural double-stranded nucleic acids in an array, wherein the double-stranded nucleic acids are at least about 152 bp, thereby generating a plurality of denatured nucleic acids, wherein each nucleic acid is present in a solution, wherein the double-stranded nucleic acids do not include a GC-clamp, and wherein the nucleic acid concentrations of the solutions are substantially the same;
  allowing the plurality of denatured nucleic acids to reanneal, thereby generating a plurality of reannealed nucleic acids;
  increasing the temperature of the plurality of reannealed nucleic acids at a rate of about 0.067° C./minute or less;
  detecting a transition of the plurality of reannealed nucleic acids between a double-stranded state and a single-stranded state, thereby generating a melting profile for the plurality of reannealed nucleic acids; and
  comparing the melting profiles of the plurality of reannealed nucleic acids, wherein a difference among the melting profiles indicates a sequence variation within the plurality of nucleic acids in the array.

23. The method according to claim 22 wherein at least one nucleic acid in the array is a homoduplex nucleic acid.

24. The method according to claim 22, further comprising amplifying the nucleic acids.

25. The method according to claim 22 wherein at least one nucleic acid in the array has a GC content of less than about 50%.

26. The method according to claim 25 wherein a majority of the nucleic acids in the array each have a GC content of less than about 50%.

27. The method according to claim 22 wherein detecting the transition comprises fluorescence detection by:
  adding a fluorescent dye to each solution; and
  detecting a fluorescent signal emitted from each solution, wherein a difference between or among the fluorescent signals emitted from the solutions at the same temperature indicates a difference between or among the melting profiles of the nucleic acids in the array.

28. The method of claim 1, wherein the first double-stranded nucleic acid is about 150 to about 180 bp in length.

29. The method of claim 28, wherein the second double-stranded nucleic acid is about 152 to about 180 bp in length.

30. The method of claim 1, wherein the first double-stranded nucleic acid is about 152 to about 1000 bp in length.

31. The method of claim 30, wherein the second double-stranded nucleic acid is about 152 to about 1000 bp in length.

32. The method of claim 1, wherein the concentration of first double-stranded nucleic acid in the solution comprising the denatured nucleic acids is substantially the same as the concentration of the second double-stranded nucleic acid in the solution comprising the denatured nucleic acids.

33. The method according to claim 1, wherein the nucleic acid sequence variation is an inversion.

34. The method of claim 1, wherein the first double-stranded nucleic acid and the second double-stranded nucleic acid are on a solid substrate.

35. A method of detecting a nucleic acid sequence variation, wherein the sequence variation is a single-nucleotide polymorphism or a 1 nucleotide deletion, insertion or inversion, comprising:
  denaturing a first double-stranded nucleic acid of at least about 152 bp, wherein the first double-stranded nucleic acid does not include a GC-clamp, thereby generating a first denatured nucleic acid in a first solution;
  denaturing a second double-stranded nucleic acid of at least about 152 bp, wherein the second double-stranded nucleic acid does not include a GC-clamp, thereby generating a second denatured nucleic acid in a second solution, wherein the nucleic acid concentration of the first solution differs from the nucleic acid concentration of the second solution by a coefficient of variation of less than about 5%;
  allowing the first denatured nucleic acid to reanneal, thereby generating a first reannealed nucleic acid;
  allowing the second denatured nucleic acid to reanneal, thereby generating a second reannealed nucleic acid;
  denaturing the first and second reannealed nucleic acid by increasing temperature at a rate of 0.067° C./minute or less, thereby generating a melting profile for a denatured first reannealed nucleic acid and a melting profile for a denatured second reannealed nucleic acid; and
  comparing the melting profile of the denatured first reannealed nucleic acid and the denatured second reannealed nucleic acid, wherein a difference between the melting profile of the denatured first reannealed nucleic acid and the melting profile of the denatured second reannealed nucleic acid indicates a sequence variation between the first double-stranded and second double-stranded nucleic acids.

36. A method of detecting a nucleic acid sequence variation, wherein the sequence variation is a single-nucleotide polymorphism or a 1 nucleotide deletion, insertion or inversion, comprising:
  denaturing a first double-stranded nucleic acid, wherein the first double-stranded nucleic acid is at least about 152 bp, and wherein the first double-stranded nucleic acid does not include a GC-clamp, thereby generating a first denatured nucleic acid in a first solution;
  denaturing a second double-stranded nucleic acid, wherein the second double-stranded nucleic acid is at least about 152 bp, and wherein the second double-stranded nucleic acid does not include a GC-clamp, thereby generating a second denatured nucleic acid in a second solution;
  allowing the first denatured nucleic acid to reanneal, thereby generating a first reannealed nucleic acid;
  allowing the second denatured nucleic acid to reanneal, thereby generating a second reannealed nucleic acid;
  increasing the temperature of the first and second reannealed nucleic acid at a rate of 0.067° C./minute or less;
  detecting a transition of the first and second reannealed nucleic acid between a double-stranded state and a single-stranded state, thereby generating a melting profile for the first and second reannealed nucleic acid; and
  comparing the melting profiles of the first and second reannealed nucleic acids wherein a difference between the melting profiles of the first reannealed nucleic acid and the melting profile of the second reannealed nucleic acid indicates a sequence variation between the first double-stranded and second double- stranded nucleic acids.

37. The method according to claim 36, wherein detecting the transition comprises fluorescence detection by:
  adding a fluorescent dye to the first and the second solution; and
  detecting a fluorescent signal emitted from the first and the second solution, wherein a difference between or among the fluorescent signals emitted from the first and the second solutions at the same temperature indicates a difference between or among the melting profiles of the first and the second reannealed nucleic acids.

38. The method of claim 37, wherein the concentration of fluorescent dye in the first solution is substantially the same as the concentration of fluorescent dye in the second solution.

39. The method of claim 1, wherein the first double-stranded nucleic acid comprises a first copy of a gene obtained from a subject and the second double-stranded nucleic acid comprises a second copy of the gene obtained from a subject.

40. A method of detecting a mutation correlated with a genetic disease in a subject, comprising:
   detecting a nucleic acid sequence variation according to the method of claim 36, wherein the first double-stranded nucleic acid comprises a wild-type sequence and the second double-stranded nucleic acid has been obtained from the subject, and wherein a difference in melting profiles between the first reannealed nucleic acid and the second reannealed nucleic acid indicates a mutation in the second double-stranded nucleic acid that is correlated with a genetic disease.

41. The method according to claim 40 wherein the genetic disease is sickle cell anemia, diabetes, Alzheimer's disease, Huntington's disease, breast cancer retinoblastoma, cystic fibrosis, Factor VIII hemophilia, Duchenne/Becker muscular dystrophy, Type 1 von Willebrand disease, familial Alzheimer's disease, familial hypercholesterolaemia, or a disease resulting from a mutation in nucleic acid encoding the low-density lipoprotein receptor.

42. The method according to claim 40 wherein the subject is a mammal.

43. The method according to claim 42 wherein the mammal is a human.

44. The method according to claim 40, wherein the nucleic acid concentration of the first double stranded nucleic acid differs from the nucleic acid concentration of the second double stranded nucleic acid by a coefficient of variation of less than about 5%.

* * * * *

UNITED STATES PATENT AND TRADEMARK OFFICE
CERTIFICATE OF CORRECTION

PATENT NO. : 7,273,699 B2 Page 1 of 1
APPLICATION NO. : 10/206561
DATED : September 25, 2007
INVENTOR(S) : Lipsky et al.

It is certified that error appears in the above-identified patent and that said Letters Patent is hereby corrected as shown below:

Column 31, line 2, claim 22, "away" should be --array--.

Column 31, line 45, claim 28, "150" should be --152--.

Signed and Sealed this

Third Day of June, 2008

JON W. DUDAS
*Director of the United States Patent and Trademark Office*